United States Patent
Issa et al.

(10) Patent No.: US 10,513,516 B2
(45) Date of Patent: Dec. 24, 2019

(54) AMINOTHIAZOLE COMPOUNDS AND METHODS USING SAME

(71) Applicant: Temple University—Of The Commonwealth System of Higher Education, Philadelphia, PA (US)

(72) Inventors: Jean-Pierre J. Issa, Philadelphia, PA (US); Hanghang Zhang, Philadelphia, PA (US); Magid Abu-Gharbia, Exton, PA (US); Wayne E. Childers, New Hope, PA (US); George C. Morton, Collegeville, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 15/746,838

(22) PCT Filed: Jul. 21, 2016

(86) PCT No.: PCT/US2016/043379
§ 371 (c)(1),
(2) Date: Jan. 23, 2018

(87) PCT Pub. No.: WO2017/015484
PCT Pub. Date: Jan. 26, 2017

(65) Prior Publication Data
US 2018/0215750 A1    Aug. 2, 2018

Related U.S. Application Data

(60) Provisional application No. 62/196,088, filed on Jul. 23, 2015.

(51) Int. Cl.
| | | |
|---|---|---|
| C07D 417/06 | (2006.01) | |
| C07D 417/14 | (2006.01) | |
| A61K 31/427 | (2006.01) | |
| A61K 45/06 | (2006.01) | |
| A61K 31/706 | (2006.01) | |
| A61P 35/00 | (2006.01) | |

(52) U.S. Cl.
CPC .......... *C07D 417/14* (2013.01); *A61K 31/427* (2013.01); *A61K 31/706* (2013.01); *A61K 45/06* (2013.01); *A61P 35/00* (2018.01); *C07D 417/06* (2013.01); *A61K 2300/00* (2013.01)

(58) Field of Classification Search
CPC .............................. C07D 417/06; C07D 417/14
See application file for complete search history.

(56) References Cited

U.S. PATENT DOCUMENTS

| 6,613,753 B2 | 9/2003 | Rubinfeld |
| 2007/0167329 A1* | 7/2007 | Bastiaans ............... A01N 43/78 504/235 |
| 2009/0286793 A1 | 11/2009 | Ibrahim |
| 2010/0129363 A1 | 5/2010 | Zeldis |

FOREIGN PATENT DOCUMENTS

| WO | 2005063022 A1 | 7/2005 |
| WO | 2005103034 A1 | 11/2005 |
| WO | 2008083098 A1 | 7/2008 |

OTHER PUBLICATIONS

Kelly et al., "Epigenetic Modifications as Therapeutic Targets", Nat. Biotechnol., 2010, 28:1069-1078.
Taby et al., "Cancer Epigenetics", 2010, CA Cancer J. Clin., 60:376-392.
Baylin et al, "A decade of exploring the cancer epigenome—biological and translational implications", 2011, Nat. Rev. Cancer, 11:726-734.
Juergens et al., "Combination Epigenetic Therapy Has Efficacy in Patients with Refractory Advanced Non-Small Cell Lung Cancer", 2011, Cancer Discov., 1:589-607.
Arrowsmith et al., "Epigenetic protein families: a new frontier for drug discovery", 2012, Nat. Rev. Drug Discov., 11:384-400.
Si et al., "Chromatin remodeling is required for gene reactivation after decitabine-mediated DNA hypomethylation", 2010, Cancer Res., 70:6968-6977.
Raynal et al., "DNA methylation does not stably lock gene expression but instead serves as a molecular mark for gene silencing memory", 2012, Cancer Res., 72:1170-1181.
Wu et al., "Histone deacetylase inhibitor depsipeptide activates silenced genes through decreasing both CpG and H3K9 methylation on the promoter", 2008, Mol. Cell Biol., 28:3219-3235.
PubChem CID-53297996, Create Date: Aug. 2, 2011, p. 3, Figure.

(Continued)

*Primary Examiner* — Brian E McDowell
(74) *Attorney, Agent, or Firm* — Riverside Law LLP

(57) ABSTRACT

The present invention includes novel aminothiazole compounds of formula (I)

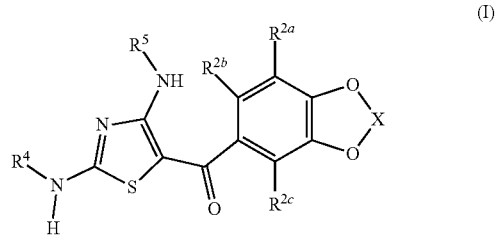

useful in preventing or treating cancer in a subject in need thereof. The present invention also includes methods of preventing or treating cancer in a subject in need thereof by administering to the subject a therapeutically effective amount of a compound of the invention.

5 Claims, No Drawings

(56) References Cited

OTHER PUBLICATIONS

Sharlow, E. R. et al., "Development and Implementation of a Miniaturized High-Throughput Time-Resolved Fluorescence Energy Transfer Assay to Identify Small Molecule Inhibitors of Polo-Like Kinase 1", Assay and Drug Development Technologies, 2007, 5:723-736.

* cited by examiner

AMINOTHIAZOLE COMPOUNDS AND METHODS USING SAME

CROSS-REFERENCE TO RELATED APPLICATIONS

This application is the U.S. national phase application filed under 35 U.S.C. § 371 claiming benefit to International Patent Application No. PCT/US2016/043379, filed Jul. 21, 2016, which is entitled to priority under 35 U.S.C. § 119(e) to U.S. Provisional Patent Application Ser. No. 62/196,088, filed Jul. 23, 2015, the entire contents of all of which are incorporated herein by reference.

STATEMENT REGARDING FEDERALLY SPONSORED RESEARCH OR DEVELOPMENT

This invention was made with U.S. government support under Grant No. CA100632 awarded by the National Institutes of Health. The U.S. government has certain rights in the invention.

BACKGROUND OF THE INVENTION

In cancer, the epigenome is aberrantly reprogrammed leading to a wide range of heritable changes in gene expression such as silencing of tumor suppressor genes (TSG) (Kelly et al., 2010, Nat. Biotechnol. 28:1069-1078). The most studied epigenetic aberrations in cancer involve DNA methylation and histone post-translational modifications. Acquisition of de novo methylation in cytosine of CpG dinucleotide at the promoter region of TSG results in stable gene silencing through direct inhibition of transcription factor binding or by recruitment of methyl-binding domain (MBD) proteins such as MeCP2 (Kelly et al., 2010, Nat. Biotechnol. 28:1069-1078; Taby and Issa, 2010, CA Cancer J. Clin. 60:376-392). These MBDs are associated with other repressor complexes including histone deacetylases (HDAC) that are responsible for global loss of histone acetylation resulting in gene silencing and heterochromatin formation (Taby and Issa, 2010, CA Cancer J. Clin. 60:376-392).

Since these epigenetic modifications are reversible, one goal of epigenetic therapy of cancer is to reverse these alterations and induce TSG reactivation leading to cancer cell differentiation and cancer cell death (Baylin and Jones, 2011, Nat. Rev. Cancer 11:726-734). Clinical efficacy of epigenetic drugs led to their approval for the treatment of hematological malignancies and occasional proof-of-principle responses can be seen in solid tumors (Taby and Issa, 2010, CA Cancer J. Clin. 60:376-392; Juergens et al., 2011, Cancer Discov. 589-607). However, treatment options are limited to a small number of epigenetic drugs approved in the clinic with two DNA methylation inhibitors (decitabine and azacitidine) and two HDAC inhibitors (vorinostat and depsipeptide). There is a need to discover new candidate epigenetic drugs, including some that work through other mechanisms of action. Drug discovery initiatives are underway in rare and specific cancer types with well-defined mutations in epigenetic effectors. However, these efforts may take years before approval and may have limited effects outside of a restricted patient population (Arrowsmith et al., 2012, Nat. Rev. Drug Discov. 11:384-400).

There is a need in the art to identify novel compounds which are useful for the treatment of cancer, in addition to other diseases and disorder, and do not cause deleterious side effects in the subject. The present invention fulfills this need.

BRIEF SUMMARY OF THE INVENTION

The present invention includes a compound of formula (I):

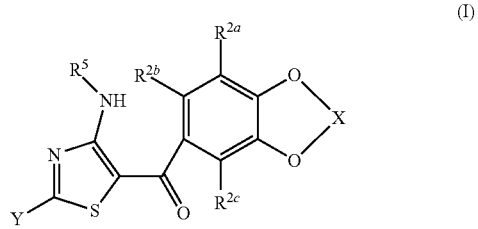

including enantiomers, diastereomers, hydrates, solvates, pharmaceutically acceptable salts, prodrugs and complexes thereof;

wherein in formula (I):

X is selected from the group consisting of

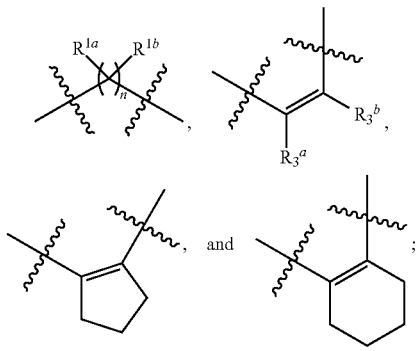

n is 1, 2, 3 or 4;

$R^{1a}$ and $R^{1b}$ are at each occurrence independently selected from the group consisting of hydrogen, $C_{1-4}$ linear alkyl, and $C_{3-6}$ branched alkyl, or $R^{1a}$ and $R^{1b}$ are taken together with the atoms to which they are bound to form a three to six membered carbocyclic ring, or two $R^{1a}$ units on adjacent carbon atoms are taken together with the atoms to which they are bound to form a three to six membered carbocyclic ring;

$R^{2a}$, $R^{2b}$, and $R^{2c}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxy, $C_{1-6}$ haloalkoxy, thiol, $C_{1-6}$ linear thioalkyl, $C_{3-6}$ branched thioalkyl, cyano, nitro, and $NH_2$;

$R^{3a}$ and $R^{3b}$ are each independently selected from the group consisting of hydrogen, $C_{1-4}$ linear alkyl, and $C_{3-6}$ branched alkyl;

$R^4$ is selected from the group consisting of $C_{1-6}$ optionally substituted linear alkyl, $C_{3-7}$ optionally substituted branched alkyl, $C_{3-10}$ optionally substituted cycloalkyl, $C_{4-9}$ optionally substituted heteroaryl, $C_{4-9}$ optionally substituted heteroarylalkyl

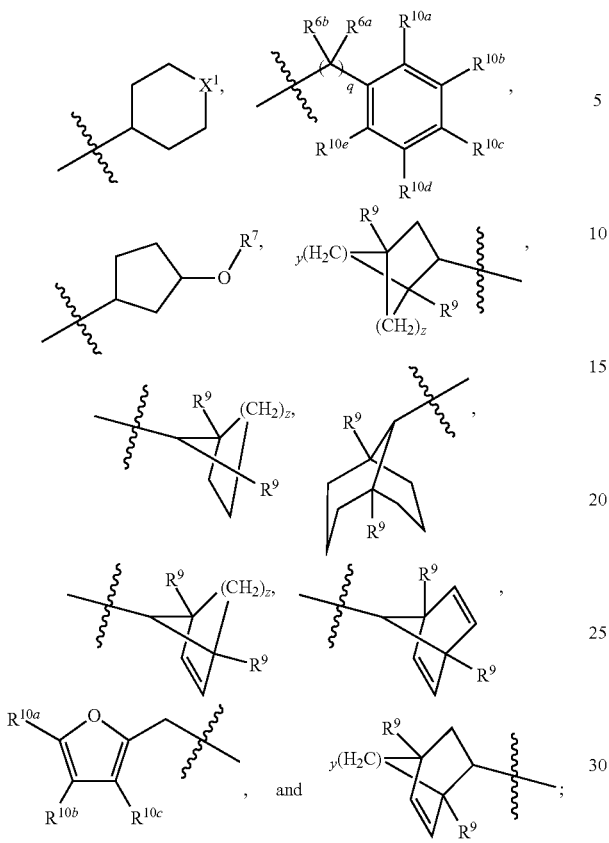

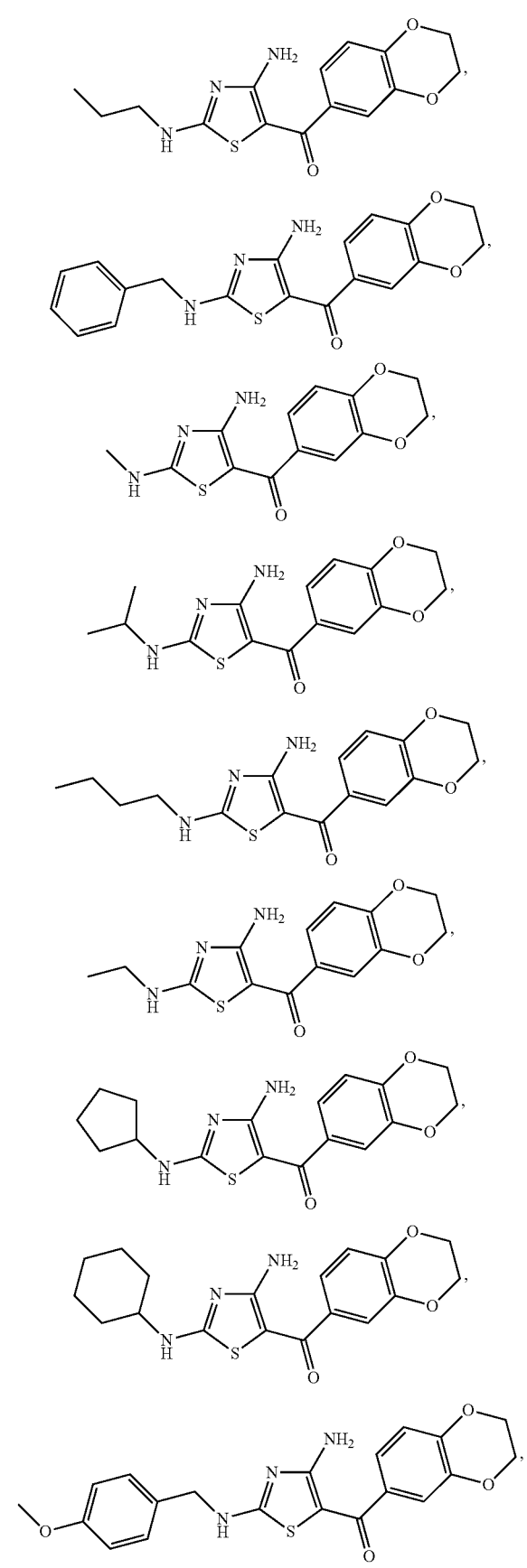

$X^1$ is selected from the group consisting of O, $NR^{11}$, S, SO, and $SO_2$;

$R^5$ is selected from the group consisting of hydrogen, $C_{1-6}$ linear alkyl, $C_{3-7}$ branched alkyl, $C_{3-7}$ cycloalkyl, and $COR^8$;

$R^{6a}$ and $R^{6b}$ are at each occurrence independently selected from the group consisting of hydrogen, $C_{1-6}$ linear alkyl, and $C_{3-6}$ branched alkyl;

q is 1 or 2;

$R^7$ is selected from the group consisting of $C_{1-6}$ linear alkyl, $C_{3-6}$ branched alkyl, $CF_3$, and $C_{1-3}$ haloalkyl;

$R^8$ is selected from the group consisting of hydrogen, $C_{1-6}$ linear alkyl, $C_{3-7}$ branched alkyl, $C_{1-6}$ linear alkoxy, $C_{3-7}$ branched alkoxy, and $C_{3-7}$ cycloalkyl;

$R^9$ at each occurrence is independently selected from the group consisting of hydrogen, methyl, ethyl, and n-propyl;

$R^{10a}$, $R^{10b}$, $R^{10c}$, $R^{10d}$, and $R^{10e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxyl, $C_{1-6}$ haloalkoxy, thiol, $C_{1-6}$ linear thioalkyl, $C_{3-6}$ branched thioalkyl, cyano, nitro, $NH_2$, and $NR^{11a}R^{11b}$;

$R^{11}$ is selected from the group consisting of hydrogen and $C_{1-6}$ linear alkyl;

$R^{11a}$ and $R^{11b}$ are each independently selected from the group consisting of $C_{1-6}$ linear alkyl and $C_{3-6}$ branched alkyl;

y is 1, 2, or 3; and z is 1, 2, or 3.

In one embodiment, the compound of formula (I) is a compound of formula (II)-(XVIII). In another embodiment, the compound of formula (I) is selected from the group consisting of:

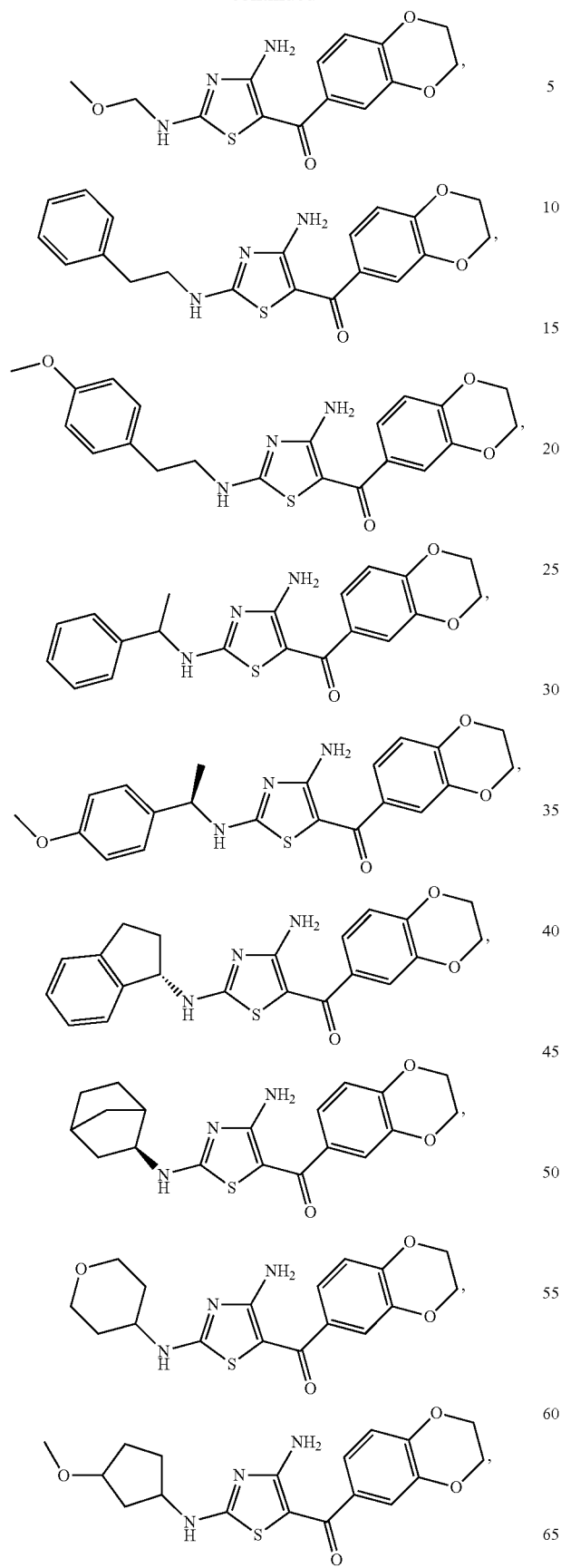
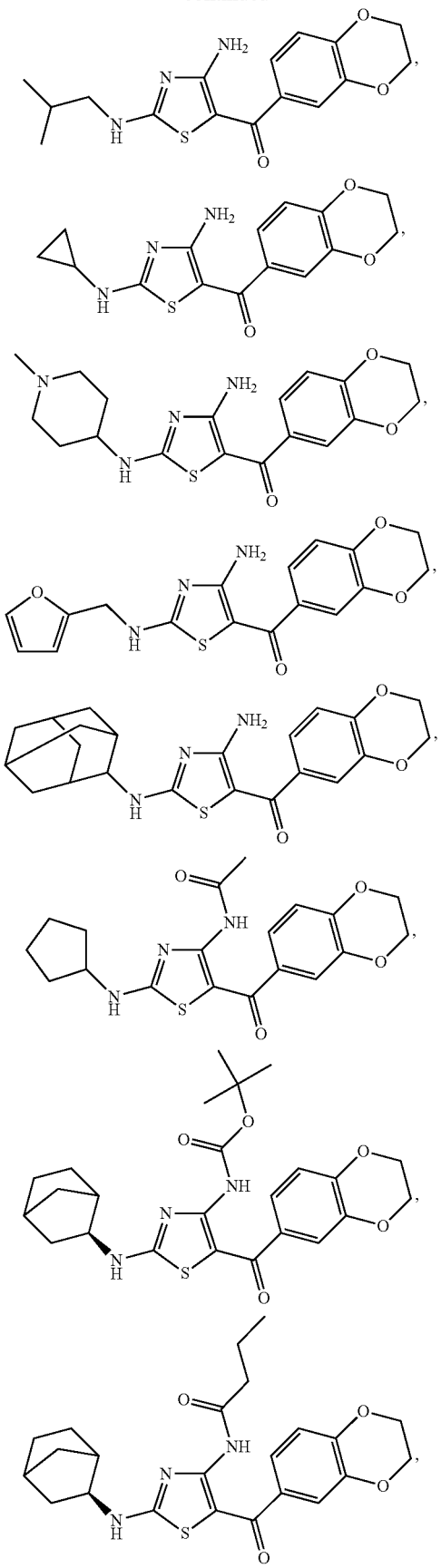

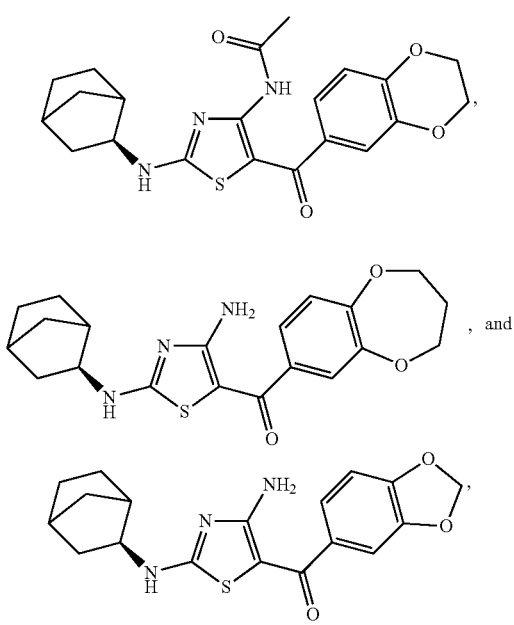

a salt or solvate thereof, and any combinations thereof.

The present invention also includes a composition comprising a compound of formula (I). In one embodiment, the composition further comprises a pharmaceutically acceptable carrier. In another embodiment, the composition further comprises an additional therapeutic agent. In another embodiment, the composition further comprises Decitabine The present invention also includes a method of preventing or treating cancer in a subject in need thereof. In one embodiment, the method includes administering to the subject a therapeutically effective amount of a composition comprising at least one compound of formula (I). In one embodiment, the cancer is selected from the group consisting of the cancer is selected from the group consisting of lung cancer, colon cancer, melanoma, breast cancer, ovarian cancer, prostate cancer, liver cancer, pancreatic cancer, a CNS tumor, neuroblastoma, leukemia, bone cancer, intestinal cancer, lymphoma, and combinations thereof. In another embodiment, the method further comprises administering to the subject at least one additional therapeutic agent. In another embodiment, the therapeutic agent is a chemotherapeutic agent. In another embodiment, the additional therapeutic agent is Decitabine. In another embodiment, the composition and the additional therapeutic agent are co-administered. In another embodiment, the composition and the additional therapeutic agent are co-formulated.

DETAILED DESCRIPTION OF THE INVENTION

This invention includes the unexpected identification of novel aminothiazole compounds that are useful as epigenetic compounds for the treatment of cancer. As demonstrated herein, compounds of the invention were found to reactivate silenced gene expression in YB5 cells and other cancer cells, including MCF7 cells. The compounds were also found to inhibit Cyclin Dependent Kinases (CDKs), and therefore the CDK inhibitors of the invention can be useful as anti-cancer compounds. The compounds of the invention are expected to have desirable pharmocokinetic and pharmacodynamic properties, and appear to be more potent than other CDK inhibitors not developed by targeting silenced tumor-suppressor genes expression.

In one embodiment, the invention provides a novel class of compounds that reactivate silenced tumor-suppressor genes in-vitro and show selective cancer cell killing. These compounds are novel epigenetic drugs having anti-cancer activity.

The present invention also includes novel methods of treating or preventing cancer using the compounds of the invention. In one embodiment, the cancer is selected from the group consisting of lung cancer, colon cancer, melanoma, breast cancer, ovarian cancer, prostate cancer, liver cancer, pancreatic cancer, CNS tumors (including brain tumors), neuroblastoma, leukemia, bone cancer, intestinal cancer, lymphoma, and combinations thereof.

The present invention includes a composition comprising at least one compound of the invention, wherein the composition optionally further comprise at least one additional therapeutic agent. In one embodiment, the additional therapeutic agent is a chemotherapeutic agent. In another embodiment, the additional therapeutic agent is decitabine (a known DNA methyltransferase (DNMT) inhibitor).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

For the purposes of the present invention the terms "compound," "analog," and "composition of matter" stand equally well for the aminothiazole compounds described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —$NH_2$, amino, azido, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

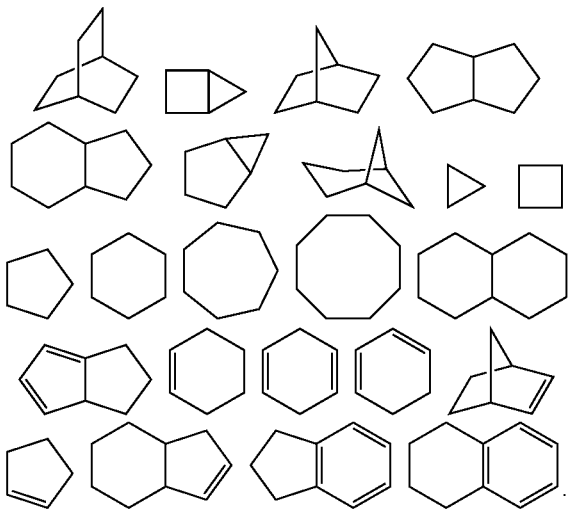

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

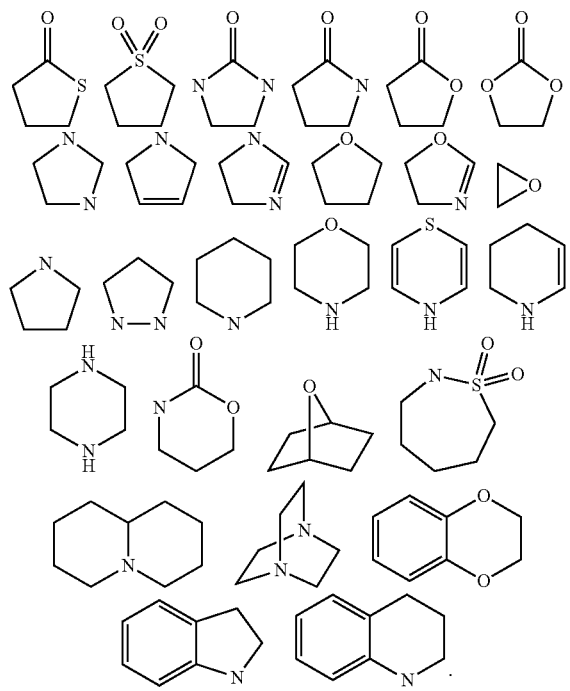

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized 2n (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

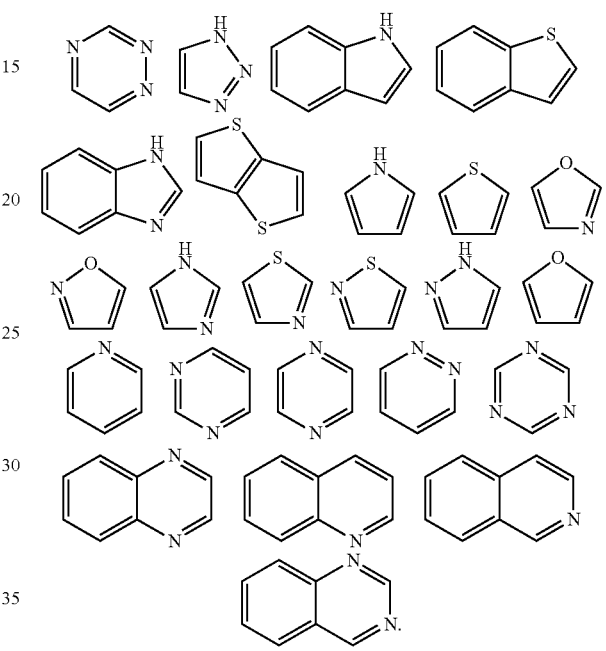

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, the term "Decitabine" refers to 4-amino-1-(2-deoxy-β-D-erythro-pentofuranosyl)-1,3,5-triazin-2 (1H)-one.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds Useful within the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I):

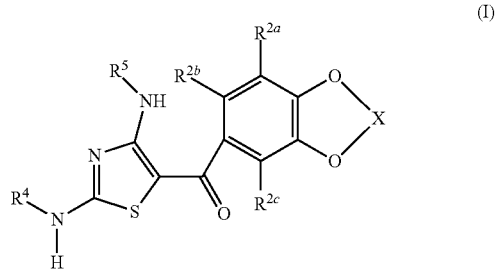

(I)

including enantiomers, diastereomers, hydrates, solvates, pharmaceutically acceptable salts, prodrugs and complexes thereof; wherein in formula (I):

X is selected from the group consisting of

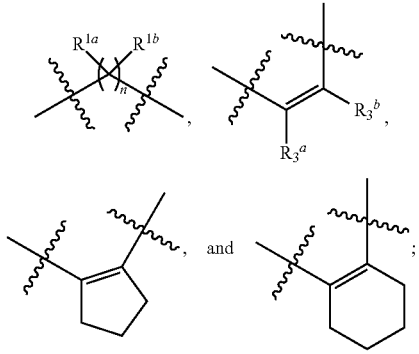

n is 1, 2, 3 or 4;

$R^{1a}$ and $R^{1b}$ are at each occurrence independently selected from the group consisting of hydrogen, C$_{1-4}$ linear alkyl, and C$_{3-6}$ branched alkyl, or $R^{1a}$ and $R^{1b}$ are taken together with the atoms to which they are bound to form a three to six membered carbocyclic ring, or two $R^{1a}$ units on adjacent carbon atoms are taken together with the atoms to which they are bound to form a three to six membered carbocyclic ring;

$R^{2a}$, $R^{2b}$, and $R^{2c}$ are each independently selected from the group consisting of hydrogen, halogen, hydroxyl, C$_{1-6}$ linear alkyl, C$_{3-6}$ branched alkyl, C$_{3-6}$ cycloalkyl, C$_{1-6}$ haloalkyl, C$_{1-6}$ linear alkoxy, C$_{3-6}$ branched alkoxy, C$_{1-6}$ haloalkoxy, thiol, C$_{1-6}$ linear thioalkyl, C$_{3-6}$ branched thioalkyl, cyano, nitro, and NH$_2$:

$R^{3a}$ and $R^{3b}$ are each independently selected from the group consisting of hydrogen, C$_{1-4}$ linear alkyl, and C$_{3-6}$ branched alkyl;

$R^4$ is selected from the group consisting of C$_{1-6}$ optionally substituted linear alkyl, C$_{3-7}$ optionally substituted branched alkyl, C$_{3-10}$ optionally substituted cycloalkyl, C$_{4-9}$ optionally substituted heteroaryl, C$_{4-9}$ optionally substituted heteroarylalkyl,

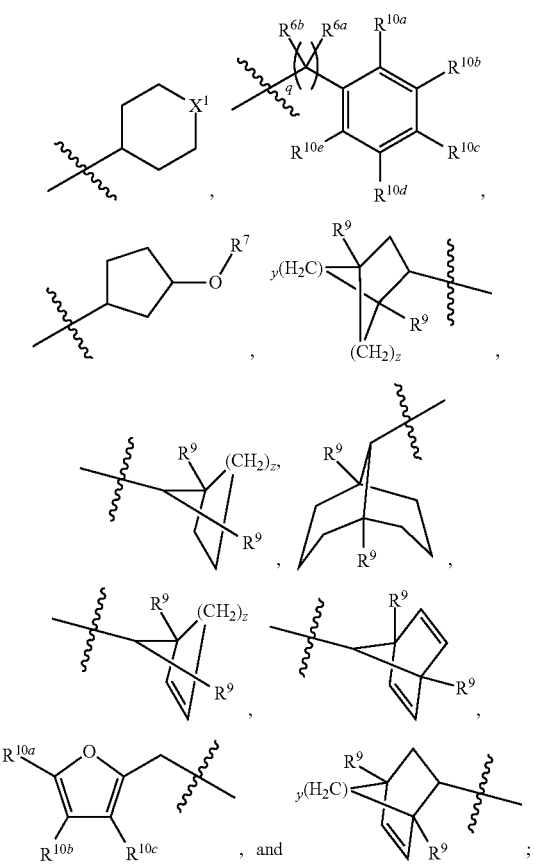

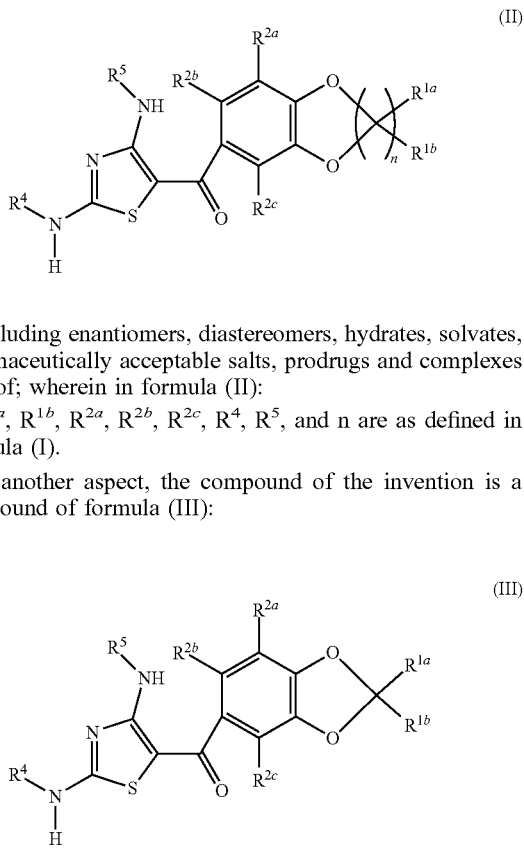

$X^1$ is selected from the group consisting of O, $NR^{11}$, S, SO, and $SO_2$;

$R^5$ is selected from the group consisting of hydrogen, $C_{1-6}$ linear alkyl, $C_{3-7}$ branched alkyl, $C_{3-7}$ cycloalkyl, and $COR^8$;

$R^{6a}$ and $R^{6b}$ are at each occurrence independently selected from the group consisting of hydrogen, $C_{1-6}$ linear alkyl, and $C_{3-6}$ branched alkyl;

q is 1 or 2;

$R^7$ is selected from the group consisting of $C_{1-6}$ linear alkyl, $C_{3-6}$ branched alkyl, $CF_3$, and $C_{1-3}$ haloalkyl;

$R^8$ is selected from the group consisting of hydrogen, $C_{1-6}$ linear alkyl, $C_{3-7}$ branched alkyl, $C_{1-6}$ linear alkoxy, $C_{3-7}$ branched alkoxy, and $C_{3-7}$ cycloalkyl;

$R^9$ at each occurrence is independently selected from the group consisting of hydrogen, methyl, ethyl, and n-propyl;

$R^{10a}$, $R^{10b}$, $R^{10c}$, $R^{10d}$, and $R^{10e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxyl, $C_{1-6}$ haloalkoxy, thiol, $C_{1-6}$ linear thioalkyl, $C_{3-6}$ branched thioalkyl, cyano, nitro, $NH_2$, and $NR^{11a}R^{11b}$;

$R^{11}$ is selected from the group consisting of hydrogen and $C_{1-6}$ linear alkyl;

$R^{11a}$ and $R^{11b}$ are each independently selected from the group consisting of $C_{1-6}$ linear alkyl and $C_{3-6}$ branched alkyl;

y is 1, 2, or 3; and z is 1, 2, or 3.

In another aspect, the compound of the invention is a compound of formula (II):

$$(II)$$

including enantiomers, diastereomers, hydrates, solvates, pharmaceutically acceptable salts, prodrugs and complexes thereof; wherein in formula (II):

$R^{1a}$, $R^{1b}$, $R^{2a}$, $R^{2b}$, $R^{2c}$, $R^4$, $R^5$, and n are as defined in formula (I).

In another aspect, the compound of the invention is a compound of formula (III):

$$(III)$$

including enantiomers, diastereomers, hydrates, solvates, pharmaceutically acceptable salts, prodrugs and complexes thereof;

wherein in formula (III):

$R^{1a}$, $R^{1b}$, $R^{2a}$, $R^{2b}$, $R^{2c}$, $R^4$, and $R^5$ are as defined in formula (I).

In another aspect, the compound of the invention is a compound of formula (IV):

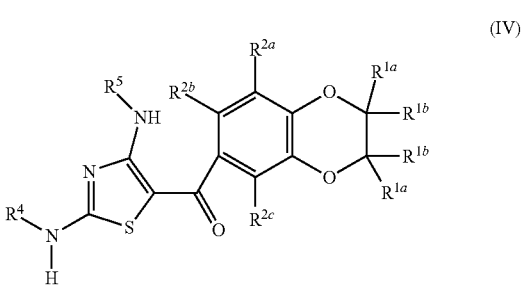

including enantiomers, diastereomers, hydrates, solvates, pharmaceutically acceptable salts, prodrugs and complexes thereof;

wherein in formula (IV):

$R^{1a}$, $R^{1b}$, $R^{2a}$, $R^{2b}$, $R^{2c}$, $R^4$, and $R^5$ are as defined in formula (I).

In another aspect, the compound of the invention is a compound of formula (V):

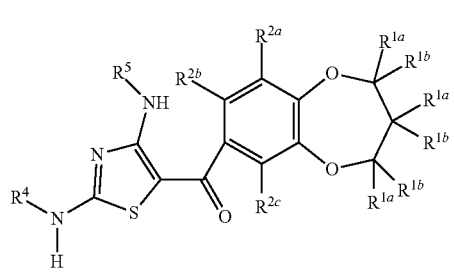

including enantiomers, diastereomers, hydrates, solvates, pharmaceutically acceptable salts, prodrugs and complexes thereof;
wherein in formula (V):
$R^{1a}$, $R^{1b}$, $R^{2a}$, $R^{2b}$, $R^{2c}$, $R^4$, and $R^5$ are as defined in formula (I).

In another aspect, the compound of the invention is a compound of formula (VI):

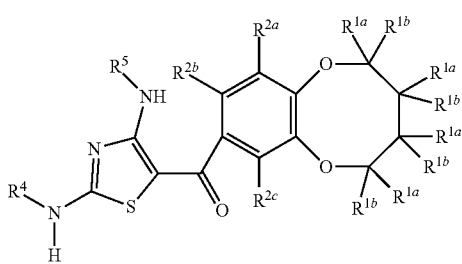

including enantiomers, diastereomers, hydrates, solvates, pharmaceutically acceptable salts, prodrugs and complexes thereof;
wherein in formula (VI):
$R^{1a}$, $R^{1b}$, $R^{2a}$, $R^{2b}$, $R^{2c}$, $R^4$, and $R^5$ are as defined in formula (I).

In another aspect, the compound of the invention is a compound of formula (VII):

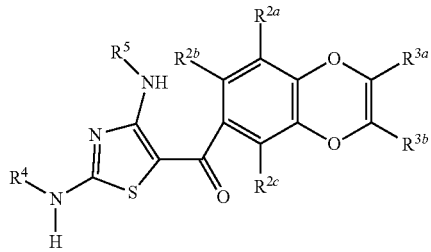

including enantiomers, diastereomers, hydrates, solvates, pharmaceutically acceptable salts, prodrugs and complexes thereof;
wherein in formula (VII):
$R^{2a}$, $R^{2b}$, $R^{2c}$, $R^{3a}$, $R^{3b}$, $R^4$, and $R^5$ are as defined in formula (I).

In another aspect, the compound of the invention is a compound of formula (VIII):

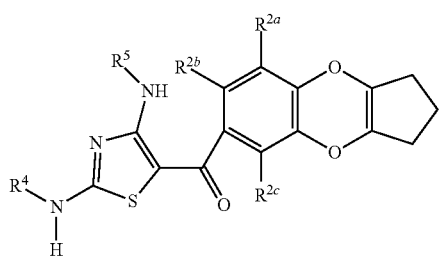

including enantiomers, diastereomers, hydrates, solvates, pharmaceutically acceptable salts, prodrugs and complexes thereof;
wherein in formula (VIII):
$R^{2a}$, $R^{2b}$, $R^{2c}$, $R^4$, and $R^5$ are as defined in formula (I).

In another aspect, the compound of the invention is a compound of formula (IX):

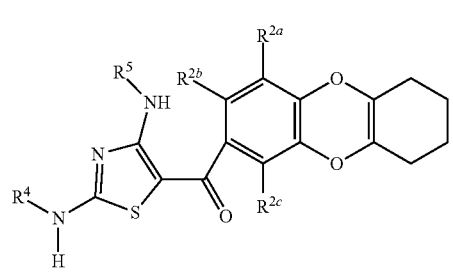

including enantiomers, diastereomers, hydrates, solvates, pharmaceutically acceptable salts, prodrugs and complexes thereof;
wherein in formula (IX):
$R^{2a}$, $R^{2b}$, $R^{2c}$, $R^4$, and $R^5$ are as defined in formula (I).

In another aspect, the compound of the invention is a compound of formula (X):

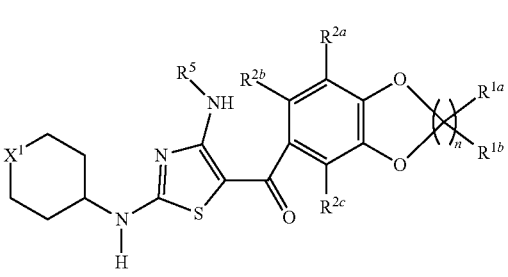

including enantiomers, diastereomers, hydrates, solvates, pharmaceutically acceptable salts, prodrugs and complexes thereof;
wherein in formula (X):
$R^{1a}$, $R^{1b}$, $R^{2a}$, $R^{2b}$, $R^{2c}$, $R^5$, $X^1$, and n are as defined in formula (I).

In another aspect, the compound of the invention is a compound of formula (XI):

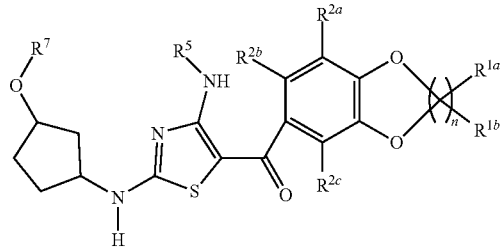

(XI)

including enantiomers, diastereomers, hydrates, solvates, pharmaceutically acceptable salts, prodrugs and complexes thereof;
wherein in formula (XI):
$R^{1a}$, $R^{1b}$, $R^{2a}$, $R^{2b}$, $R^{2c}$, $R^5$, $R^7$, and n are as defined in formula (I).

In another aspect, the compound of the invention is a compound of formula (XII):

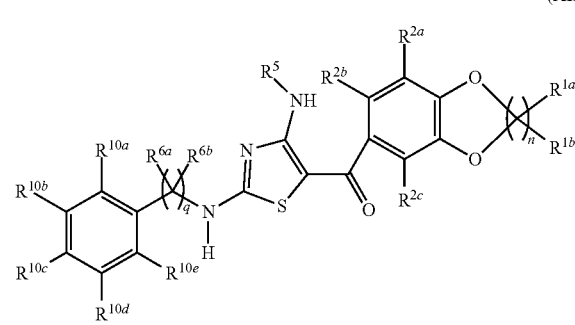

(XII)

including enantiomers, diastereomers, hydrates, solvates, pharmaceutically acceptable salts, prodrugs and complexes thereof;
wherein in formula (XII):
$R^{1a}$, $R^{1b}$, $R^{2a}$, $R^{2b}$, $R^{2c}$, $R^5$, $R^{6a}$, $R^{6b}$, $R^{10a}$, $R^{10b}$, $R^{10c}$, $R^{10d}$, $R^{10e}$ and n are as defined in formula (I).

In another aspect, the compound of the invention is a compound of formula (XIII):

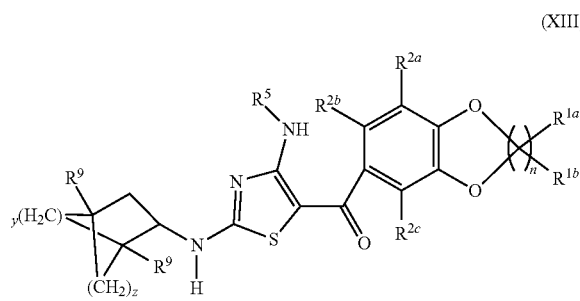

(XIII)

including enantiomers, diastereomers, hydrates, solvates, pharmaceutically acceptable salts, prodrugs and complexes thereof;

wherein in formula (XIII):
$R^{1a}$, $R^{1b}$, $R^{2a}$, $R^{2b}$, $R^{2c}$, $R^5$, $R^9$, n, y, and z are as defined in formula (I).

In another aspect, the compound of the invention is a compound of formula (XIV):

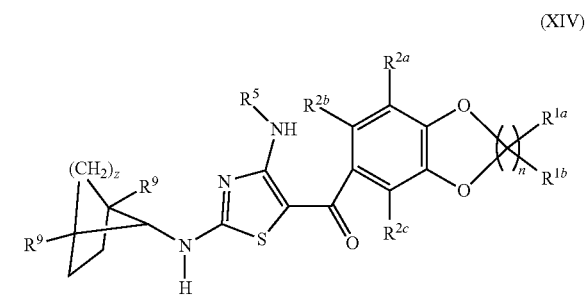

(XIV)

including enantiomers, diastereomers, hydrates, solvates, pharmaceutically acceptable salts, prodrugs and complexes thereof;
wherein in formula (XIV):
$R^{1a}$, $R^{1b}$, $R^{2a}$, $R^{2b}$, $R^{2c}$, $R^5$, $R^9$, n, and z are as defined in formula (I).

In another aspect, the compound of the invention is a compound of formula (XV):

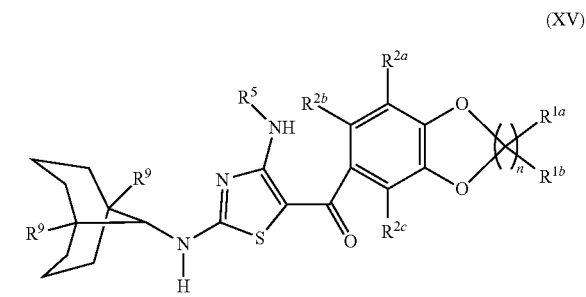

(XV)

including enantiomers, diastereomers, hydrates, solvates, pharmaceutically acceptable salts, prodrugs and complexes thereof;
wherein in formula (XV):
$R^{1a}$, $R^{1b}$, $R^{2a}$, $R^{2b}$, $R^{2c}$, $R^5$, $R^9$, and n are as defined in formula (I).

In another aspect, the compound of the invention is a compound of formula (XVI):

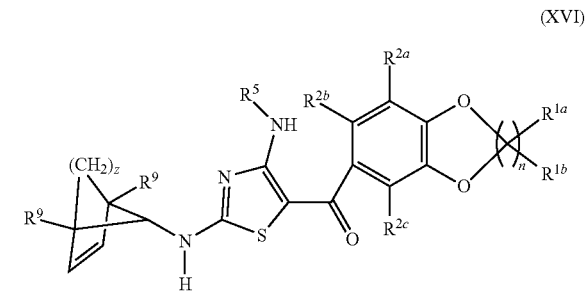

(XVI)

including enantiomers, diastereomers, hydrates, solvates, pharmaceutically acceptable salts, prodrugs and complexes thereof;

wherein in formula (XVI):
$R^{1a}$, $R^{1b}$, $R^{2a}$, $R^{2b}$, $R^{2c}$, $R^5$, $R^9$, n, and z are as defined in formula (I).

In another aspect, the compound of the invention is a compound of formula (XVII):

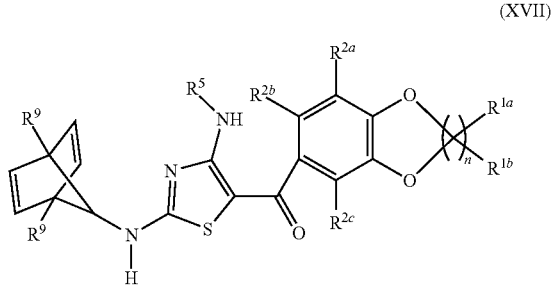

(XVII)

including enantiomers, diastereomers, hydrates, solvates, pharmaceutically acceptable salts, prodrugs and complexes thereof;
wherein in formula (XVII):
$R^{1a}$, $R^{1b}$, $R^{2a}$, $R^{2b}$, $R^{2c}$, $R^5$, $R^9$, and n are as defined in formula (I).

In another aspect, the compound of the invention is a compound of formula (XVIII):

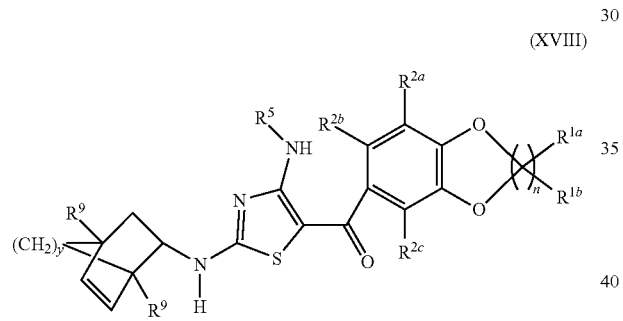

(XVIII)

including enantiomers, diastereomers, hydrates, solvates, pharmaceutically acceptable salts, prodrugs and complexes thereof;
wherein in formula (XVIII):
$R^{1a}$, $R^{1b}$, $R^{2a}$, $R^{2b}$, $R^{2c}$, $R^5$, $R^9$, n, and y are as defined in formula (I).

Compounds of the present invention include compounds having the formula (XIX) or a pharmaceutically acceptable salt form thereof:

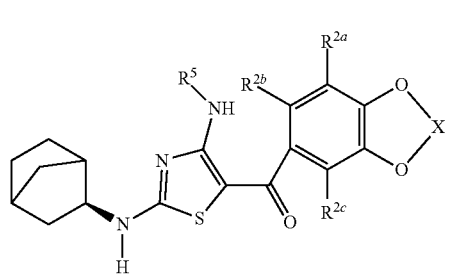

(XIX)

wherein non-limiting examples of $R^{2a}$, $R^{2b}$, $R^{2c}$, $R^5$ and X are defined herein below in Table 1.

TABLE 1

Exemplary compounds of the formula (XIX)

| Entry | $R^{2a}$ | $R^{2b}$ | $R^{2c}$ | $R^5$ | X |
|---|---|---|---|---|---|
| 1 | Cl | H | H | H | —(CH$_2$)$_2$— |
| 2 | Et | Cl | H | H | —(CH$_2$)$_2$— |
| 3 | Et | H | Cl | H | —(CH$_2$)$_2$— |
| 4 | Cl | H | Cl | H | —(CH$_2$)$_2$— |
| 5 | F | H | H | H | —(CH$_2$)$_2$— |
| 6 | H | F | H | H | —(CH$_2$)$_2$— |
| 7 | H | H | F | H | —(CH$_2$)$_2$— |
| 8 | F | H | F | H | —(CH$_2$)$_2$— |
| 9 | F | F | F | H | —(CH$_2$)$_2$— |
| 10 | CF$_3$ | H | H | H | —(CH$_2$)$_2$— |
| 11 | H | CF$_3$ | H | H | —(CH$_2$)$_2$— |
| 12 | H | H | CF$_3$ | H | —(CH$_2$)$_2$— |
| 13 | CN | H | H | H | —(CH$_2$)$_2$— |
| 14 | H | CN | H | H | —(CH$_2$)$_2$— |
| 15 | H | H | CN | H | —(CH$_2$)$_2$— |
| 16 | CF$_3$ | H | H | H | —(CH$_2$)$_2$— |
| 17 | H | CF$_3$ | H | H | —(CH$_2$)$_2$— |
| 18 | H | H | CF$_3$ | H | —(CH$_2$)$_2$— |
| 19 | OCF$_3$ | H | H | H | —(CH$_2$)$_2$— |
| 20 | H | OCF$_3$ | H | H | —(CH$_2$)$_2$— |
| 21 | H | H | OCF$_3$ | H | —(CH$_2$)$_2$— |

Compounds of the present invention include compounds having the formula (XX) or a pharmaceutically acceptable salt form thereof:

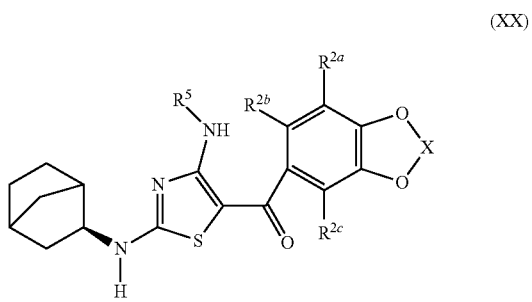

(XX)

wherein non-limiting examples of $R^{2a}$, $R^{2b}$, $R^{2c}$, $R^5$ and X are defined herein below in Table 2.

TABLE 2

Exemplary compounds of the formula (XX)

| Entry | $R^{2a}$ | $R^{2b}$ | $R^{2c}$ | $R^5$ | X |
|---|---|---|---|---|---|
| 1 | H | H | H | H | —CH$_2$— |
| 2 | H | H | H | H | —(CH$_2$)$_2$— |
| 3 | H | H | H | H | —(CH2)$_3$— |
| 4 | H | H | H | H | —(CH$_2$)$_4$— |
| 5 | H | H | H | H | —CH=CH— |
| 6 | H | H | H | H | (C(Me)=C(Me) group) |
| 7 | H | H | H | H | (dimethylcyclopentyl group) |

TABLE 2-continued

Exemplary compounds of the formula (XX)

| Entry | $R^{2a}$ | $R^{2b}$ | $R^{2c}$ | $R^5$ | X |
|---|---|---|---|---|---|
| 8 | H | H | H | H | (1,2-dimethylcyclopentenyl) |
| 9 | H | H | H | H | (cyclohexyl with gem substitution) |
| 10 | H | H | H | H | (cyclohexenyl with gem substitution) |
| 11 | H | H | H | H | (C(Me)(Me) with two bonds) |
| 12 | H | H | H | H | (C(Me)(Me)-C(Me)(Me)) |
| 13 | H | H | H | H | (spiro cyclopentyl) |

Compounds of the present invention include compounds having the formula (XXI) or a pharmaceutically acceptable salt form thereof:

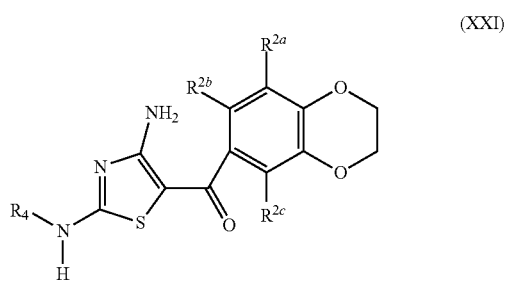

(XXI)

wherein non-limiting examples of $R^{2a}$, $R^{2b}$, $R^{2c}$, $R^5$ and X are defined herein below in Table 3.

TABLE 3

Exemplary compounds of the formula (XXI)

| Entry | $R^{2a}$ | $R^{2b}$ | $R^{2c}$ | $R^4$ |
|---|---|---|---|---|
| 1 | H | H | H | (norbornyl) |
| 2 | H | H | H | (norbornyl, Me) |
| 3 | H | H | H | (norbornyl, Et) |
| 4 | H | H | H | (norbornyl, nPr) |
| 5 | H | H | H | (norbornenyl) |
| 6 | H | H | H | (bicyclo[2.2.2]octyl) |
| 7 | H | H | H | (bicyclo[2.2.2]octyl, Me) |
| 8 | H | H | H | (bicyclic, Me, Me) |
| 9 | H | H | H | (bicyclo[2.2.2]octenyl) |
| 10 | H | H | H | (bicyclopentyl) |
| 11 | H | H | H | (cyclohexyl) |

TABLE 3-continued

Exemplary compounds of the formula (XXI)

| Entry | $R^{2a}$ | $R^{2b}$ | $R^{2c}$ | $R^4$ |
|---|---|---|---|---|
| 12 | H | H | H |  |
| 13 | H | H | H |  |

Compounds of the present invention include compounds having the formula (XXII) or a pharmaceutically acceptable salt form thereof:

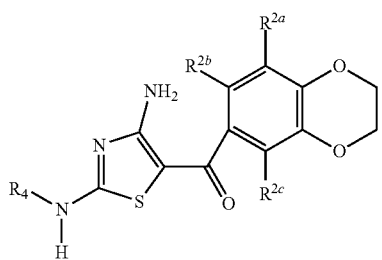

(XXII)

wherein non-limiting examples of $R^{2a}$, $R^{2b}$, $R^{2c}$, $R^5$ and X are defined herein below in Table 4.

TABLE 4

Exemplary compounds of the formula (XXII)

| Entry | $R^{2a}$ | $R^{2b}$ | $R^{2c}$ | $R^4$ |
|---|---|---|---|---|
| 1 | H | H | H | |
| 2 | H | H | H | |
| 3 | H | H | H | |
| 4 | H | H | H | |
| 5 | H | H | H | |
| 6 | H | H | H | |
| 7 | H | H | H | |
| 8 | H | H | H | |
| 9 | H | H | H | |
| 10 | H | H | H | |
| 11 | H | H | H | |
| 12 | H | H | H | |

Compounds of the present invention include compounds having the formula (XXIII) or a pharmaceutically acceptable salt form thereof:

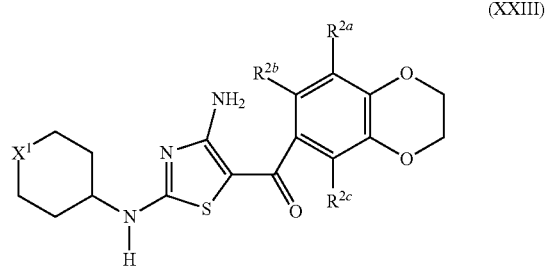

(XXIII)

wherein non-limiting examples of $R^{2a}$, $R^{2b}$, $R^{2c}$, $R^5$ and X are defined herein below in Table 5.

TABLE 5

Exemplary compounds of the formula (XXIII)

| Entry | $R^{2a}$ | $R^{2b}$ | $R^{2c}$ | $X^1$ |
|---|---|---|---|---|
| 1 | H | H | H | O |
| 2 | H | H | H | S |
| 3 | H | H | H | S=O |
| 4 | H | H | H | O=S=O |
| 5 | H | H | H | NH |
| 6 | H | H | H | N—Me |
| 7 | H | H | H | N—$C_2H_5$ |
| 8 | H | H | H | N—$nC_3H_7$ |
| 9 | H | H | H | N—$nC_4H_9$ |
| 10 | H | H | H | N—$nC_5H_{11}$ |
| 11 | H | H | H | N—$nC_6H_{13}$ |

Compounds of the present invention include compounds having the formula (XXIV) or a pharmaceutically acceptable salt form thereof:

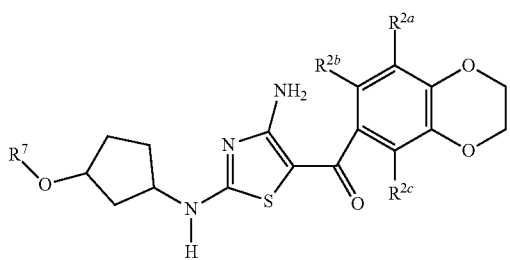

(XXIV)

wherein non-limiting examples of $R^{2a}$, $R^{2b}$, $R^{2c}$, $R^5$ and X are defined herein below in Table 6.

TABLE 6

Exemplary compounds of the formula (XXIV)

| Entry | $R^{2a}$ | $R^{2b}$ | $R^{2c}$ | $R^7$ |
|---|---|---|---|---|
| 1 | H | H | H | —$CH_3$ |
| 2 | H | H | H | —$C_2H_5$ |
| 3 | H | H | H | -$nC_3H_7$ |
| 4 | H | H | H | -$nC_4H_9$ |
| 5 | H | H | H | -$nC_5H_{11}$ |
| 6 | H | H | H | -$nC_6H_{13}$ |
| 7 | H | H | H | -iPr |
| 8 | H | H | H | -iBu |
| 8 | H | H | H | -sec-Bu |
| 10 | H | H | H | -tBu |
| 11 | H | H | H | (4-methylpentan-2-yl) |
| 12 | H | H | H | (3-methylpentyl) |
| 13 | H | H | H | (2,2-dimethylbutyl) |
| 14 | H | H | H | (3-methylpentan-2-yl) |
| 15 | H | H | H | (3-ethylpentyl) |
| 16 | H | H | H | (3-methylhexyl) |
| 17 | H | H | H | (3,4-dimethylpentyl) |
| 18 | H | H | H | (3-ethylpentan-2-yl) |
| 19 | H | H | H | (5-methylhexyl) |
| 20 | H | H | H | (3,4-dimethylpentan-2-yl) |
| 21 | H | H | H | (4,4-dimethylpentyl) |
| 22 | H | H | H | —$CF_3$ |
| 23 | H | H | H | —$CH_2CH_2F$ |
| 24 | H | H | H | —$CH_2CHF_2$ |
| 25 | H | H | H | —$CH_2CF_3$ |
| 26 | H | H | H | —$CH_2CF_2CHF_2$ |
| 27 | H | H | H | —$CH_2CF_2CF_3$ |
| 28 | H | H | H | (1-CHF$_2$, 2-CF$_3$ branched) |
| 29 | H | H | H | (1-CF$_3$, 2-CF$_3$ branched) |

Compounds of the present invention include compounds having the formula (XXV) or a pharmaceutically acceptable salt form thereof:

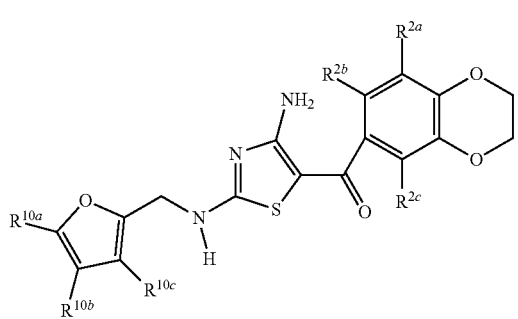

(XXV)

wherein non-limiting examples of $R^{2a}$, $R^{2b}$, $R^{2c}$, $R^5$ and X are defined herein below in Table 7.

TABLE 7

Exemplary compounds of the formula (XXV)

| Entry | $R^{2a}$ | $R^{2b}$ | $R^{2c}$ | $R^{10a}$ | $R^{10b}$ | $R^{10c}$ |
|---|---|---|---|---|---|---|
| 1 | H | H | H | H | H | H |
| 2 | H | H | H | F | H | H |
| 3 | H | H | H | Cl | H | H |
| 4 | H | H | H | Br | H | H |
| 5 | H | H | H | I | H | H |
| 6 | H | H | H | Me | H | H |
| 7 | H | H | H | Et | H | H |
| 8 | H | H | H | nPr | H | H |
| 9 | H | H | H | iPr | H | H |
| 10 | H | H | H | tBu | H | H |
| 11 | H | H | H | CN | H | H |
| 12 | H | H | H | CHF$_2$ | H | H |
| 13 | H | H | H | CF$_3$ | H | H |
| 14 | H | H | H | NO$_2$ | H | H |
| 15 | H | H | H | NH$_2$ | H | H |
| 16 | H | H | H | NMe$_2$ | H | H |
| 17 | H | H | H | O—Me | H | H |
| 18 | H | H | H | O—Et | H | H |
| 19 | H | H | H | O—iPr | H | H |
| 20 | H | H | H | O—tBu | H | H |
| 21 | H | H | H | S—Me | H | H |
| 22 | H | H | H | S—Et | H | H |
| 23 | H | H | H | S—iPr | H | H |
| 24 | H | H | H | S—tBu | H | H |
| 25 | H | H | H | H | F | H |
| 26 | H | H | H | H | Cl | H |
| 27 | H | H | H | H | Br | H |
| 28 | H | H | H | H | Me | H |
| 29 | H | H | H | H | Et | H |
| 30 | H | H | H | H | iPr | H |

TABLE 7-continued

Exemplary compounds of the formula (XXV)

| Entry | $R^{2a}$ | $R^{2b}$ | $R^{2c}$ | $R^{10a}$ | $R^{10b}$ | $R^{10c}$ |
|---|---|---|---|---|---|---|
| 31 | H | H | H | H | CN | H |
| 32 | H | H | H | H | CF$_3$ | H |
| 33 | H | H | H | H | NO$_2$ | H |
| 34 | H | H | H | H | H | F |
| 35 | H | H | H | H | H | Cl |
| 26 | H | H | H | H | H | Br |
| 27 | H | H | H | H | H | I |
| 28 | H | H | H | H | H | Me |
| 29 | H | H | H | H | H | Et |
| 40 | H | H | H | H | H | iPr |
| 41 | H | H | H | H | H | nBu |
| 42 | H | H | H | H | H | CF$_3$ |
| 43 | H | H | H | H | H | CN |
| 44 | H | H | H | H | H | NO$_2$ |
| 45 | H | H | H | Br | Me | H |
| 46 | H | H | H | Br | H | Me |
| 47 | H | H | H | Br | Br | H |
| 48 | H | H | H | Me | Br | H |
| 49 | H | H | H | Me | H | Br |
| 50 | H | H | H | Me | Me | H |
| 51 | H | H | H | Me | H | Me |
| 52 | H | H | H | CF$_3$ | H | Me |
| 53 | H | H | H | H | Me | Br |

Compounds of the present invention include compounds having the formula (XXVI) or a pharmaceutically acceptable salt form thereof:

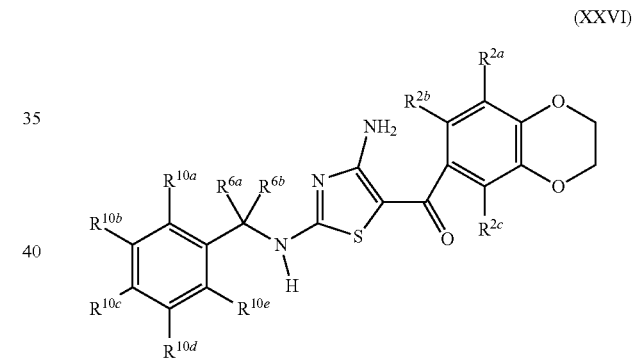

(XXVI)

wherein non-limiting examples of $R^{2a}$, $R^{2b}$, $R^{2c}$, $R^{6a}$, $R^{6b}$, $R^{10a}$, $R^{10b}$, $R^{10c}$, $R^{10d}$ and $R^{10e}$ are defined herein below in Table 8.

TABLE 8

Exemplary compounds of the formula (XXVI)

| Entry | $R^{2a}$ | $R^{2b}$ | $R^{2c}$ | $R^{6a}$ | $R^{6a}$ | $R^{10a}$ | $R^{10b}$ | $R^{10c}$ | $R^{10d}$ | $R^{10e}$ |
|---|---|---|---|---|---|---|---|---|---|---|
| 1 | H | H | H | H | H | H | H | H | H | H |
| 2 | H | H | H | H | H | F | H | H | H | H |
| 3 | H | H | H | H | H | Cl | H | H | H | H |
| 4 | H | H | H | H | H | Br | H | H | H | H |
| 5 | H | H | H | H | H | Me | H | H | H | H |
| 6 | H | H | H | H | H | OMe | H | H | H | H |
| 7 | H | H | H | H | H | CF$_3$ | H | H | H | H |
| 8 | H | H | H | H | H | OCF$_3$ | H | H | H | H |
| 9 | H | H | H | H | H | CN | H | H | H | H |
| 10 | H | H | H | H | H | NO$_2$ | H | H | H | H |
| 11 | H | H | H | H | H | NH$_2$ | H | H | H | H |
| 12 | H | H | H | H | H | NMe$_2$ | H | H | H | H |
| 13 | H | H | H | H | H | H | F | H | H | H |
| 14 | H | H | H | H | H | H | Cl | H | H | H |
| 15 | H | H | H | H | H | H | Br | H | H | H |

TABLE 8-continued

Exemplary compounds of the formula (XXVI)

| Entry | $R^{2a}$ | $R^{2b}$ | $R^{2c}$ | $R^{6a}$ | $R^{6a}$ | $R^{10a}$ | $R^{10b}$ | $R^{10c}$ | $R^{10d}$ | $R^{10e}$ |
|---|---|---|---|---|---|---|---|---|---|---|
| 16 | H | H | H | H | H | H | Me | H | H | H |
| 17 | H | H | H | H | H | H | OMe | H | H | H |
| 18 | H | H | H | H | H | H | $CF_3$ | H | H | H |
| 19 | H | H | H | H | H | H | $OCF_3$ | H | H | H |
| 20 | H | H | H | H | H | H | CN | H | H | H |
| 21 | H | H | H | H | H | H | $NO_2$ | H | H | H |
| 22 | H | H | H | H | H | H | $NH_2$ | H | H | H |
| 23 | H | H | H | H | H | H | $NMe_2$ | H | H | H |
| 24 | H | H | H | H | H | H | H | F | H | H |
| 25 | H | H | H | H | H | H | H | Cl | H | H |
| 26 | H | H | H | H | H | H | H | Br | H | H |
| 27 | H | H | H | H | H | H | H | Me | H | H |
| 28 | H | H | H | H | H | H | H | OMe | H | H |
| 29 | H | H | H | H | H | H | H | $CF_3$ | H | H |
| 30 | H | H | H | H | H | H | F | $OCF_3$ | H | H |
| 31 | H | H | H | H | H | H | Cl | CN | H | H |
| 32 | H | H | H | H | H | H | Br | $NO_2$ | H | H |
| 33 | H | H | H | H | H | H | H | $NH_2$ | H | H |
| 34 | H | H | H | H | H | H | H | $NMe_2$ | H | H |
| 35 | H | H | H | H | H | F | F | H | H | H |
| 36 | H | H | H | H | H | F | Cl | H | H | H |
| 37 | H | H | H | H | H | F | H | F | H | H |
| 38 | H | H | H | H | H | F | H | Cl | H | H |
| 39 | H | H | H | H | H | Cl | H | H | Cl | H |
| 40 | H | H | H | H | H | Cl | H | H | $CF_3$ | H |
| 41 | H | H | H | H | H | H | CN | F | Cl | H |
| 42 | H | H | H | H | H | F | H | $OCF_3$ | H | F |
| 43 | H | H | H | H | H | Me | H | F | H | OMe |
| 44 | H | H | H | H | H | H | Me | H | Me | H |
| 45 | H | H | H | H | H | Cl | H | Cl | H | Cl |
| 46 | H | H | H | H | H | H | $CF_3$ | H | $CF_3$ | H |
| 47 | H | H | H | H | H | F | H | $NO_2$ | H | H |
| 48 | H | H | H | H | H | OMe | H | OMe | H | OMe |

In one embodiment, X is

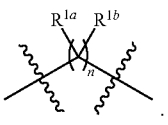

In one embodiment, n is 1.

In another embodiment, n is 2.

In another embodiment, n is 3.

In another embodiment, n is 4.

In one embodiment, $R^{1a}$ and $R^{1b}$ are each hydrogen.

In one embodiment, $R^4$ is $C_{1-6}$ optionally substituted linear alkyl.

In another embodiment, $R^4$ is $C_{3-7}$ optionally substituted branched alkyl.

In another embodiment, $R^4$ is $C_{3-7}$ branched alkyl substituted with heteroaryl.

In another embodiment, $R^4$ is $C_{3-7}$ branched alkyl substituted with $C_{1-6}$ linear alkoxy.

In another embodiment, $R^4$ is $C_{3-10}$ optionally substituted cycloalkyl.

In another embodiment, $R^4$ is $C_{4-9}$ optionally substituted heteroaryl.

In another embodiment, $R^4$ is $C_{4-9}$ optionally substituted heteroarylalkyl.

In another embodiment, $R^4$ is

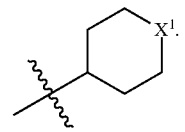

In another embodiment, $R^4$ is

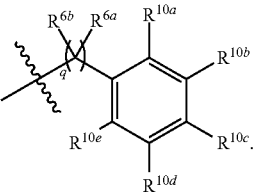

In another embodiment, $R^4$ is

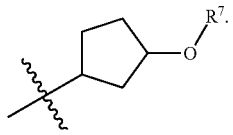

In another embodiment, $R^4$ is

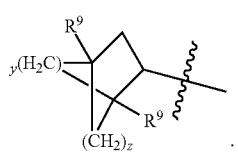

In another embodiment, $R^4$ is

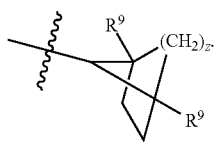

In another embodiment, $R^4$ is

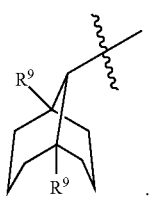

In another embodiment, $R^4$ is

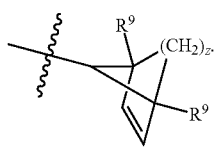

In another embodiment, $R^4$ is

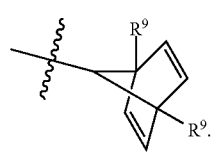

In another embodiment, $R^4$ is

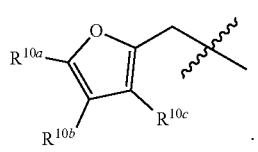

In another embodiment, $R^4$ is

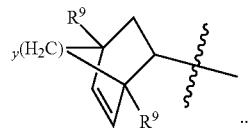

In one embodiment, $X^1$ is $NR^{11}$.
In another embodiment, $X^1$ is O.
In one embodiment, $R^5$ is hydrogen.
In another embodiment, $R^5$ is $COR^8$.
In one embodiment, $R^{6a}$ and $R^{6b}$ are at each occurrence hydrogen.
In another embodiment, one of $R^{6a}$ and $R^{6b}$ is hydrogen and the other is $C_{1-6}$ linear alkyl at each occurrence.
In one embodiment, q is 1.
In another embodiment, q is 2.
In one embodiment, $R^7$ is $C_{1-6}$ linear alkyl.
In one embodiment, $R^8$ is $C_{1-6}$ linear alkyl.
In another embodiment, $R^8$ is $C_{3-7}$ branched alkoxy.
In one embodiment, $R^9$ is hydrogen at each occurrence.
In another embodiment, $R^9$ is methyl at each occurrence.
In another embodiment, $R^9$ is ethyl at each occurrence.
In another embodiment, $R^9$ is n-propyl at each occurrence.
In another embodiment, one $R^9$ is hydrogen and one $R^9$ is methyl.
In one embodiment, $R^{10a}$, $R^{10b}$, $R^{10c}$, $R^{10d}$, and $R^{10e}$ are each hydrogen.
In another embodiment, $R^{10c}$ is $C_{1-6}$ linear alkoxy.
In one embodiment, $R^{11}$ is $C_{1-6}$ linear alkyl.
In one embodiment, y is 1.
In another embodiment, y is 2.
In another embodiment, y is 3.
In one embodiment, z is 1.
In another embodiment, z is 2.
In another embodiment, z is 3.
In one embodiment, the compound of the invention is selected from the group consisting of:

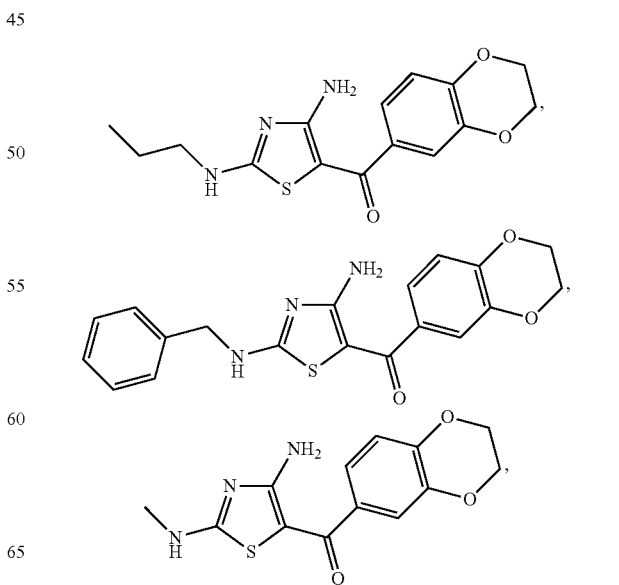

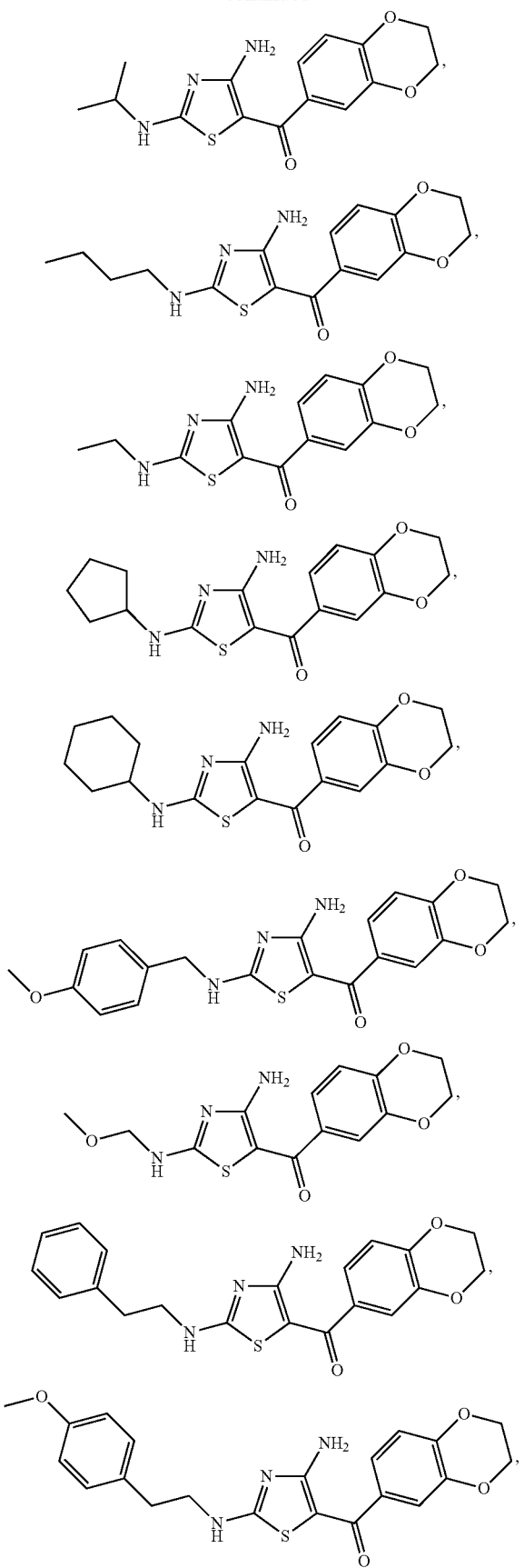
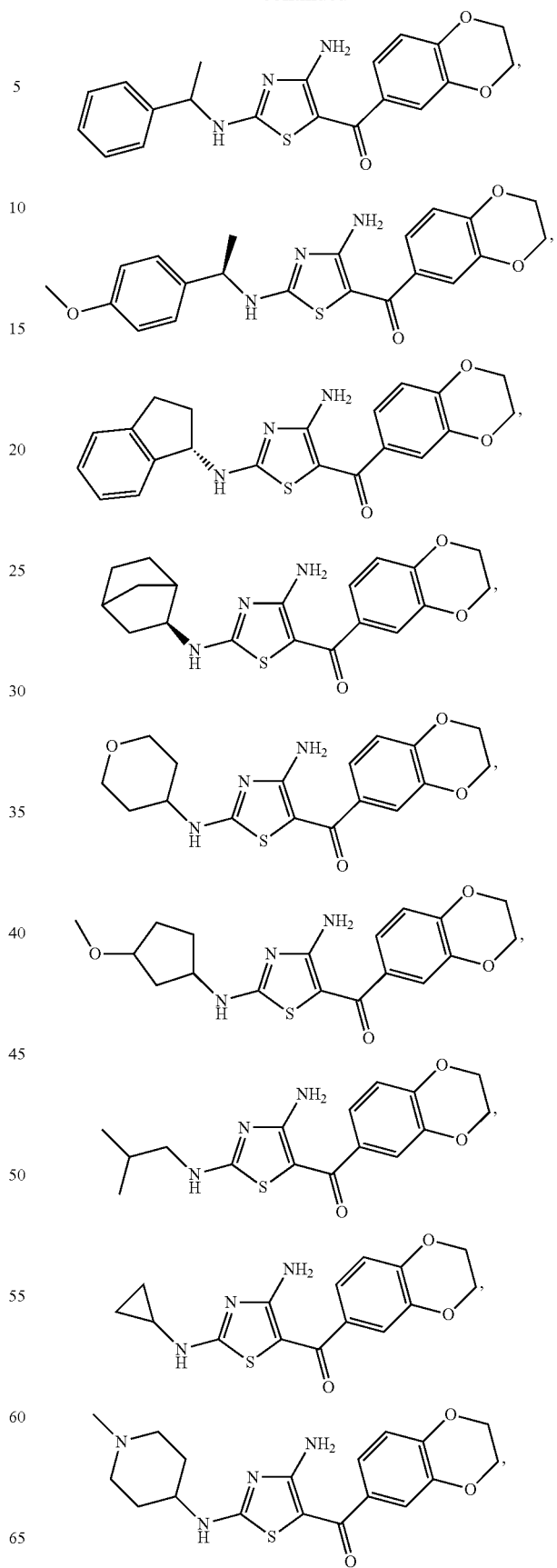

-continued

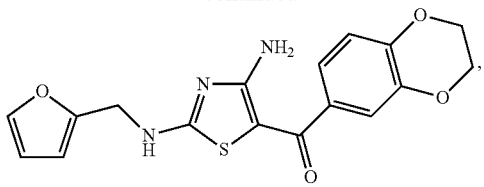

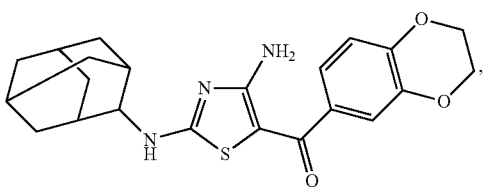

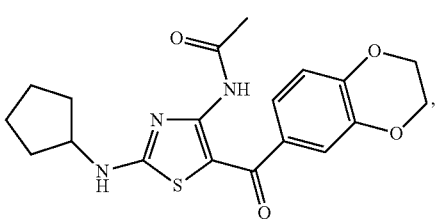

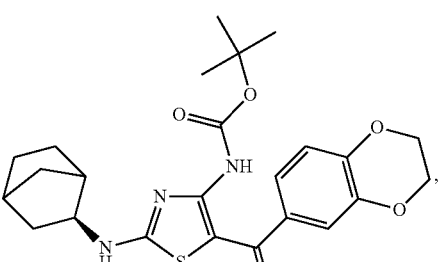

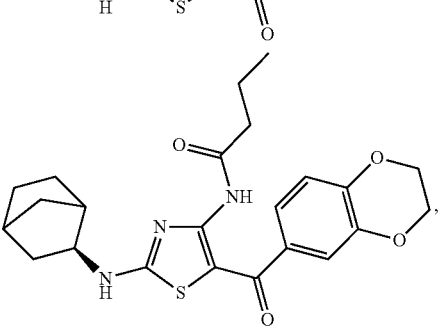

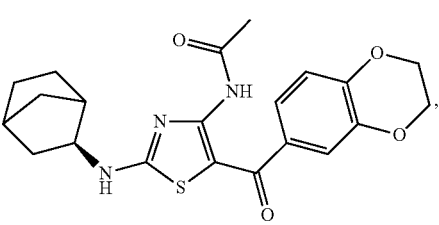

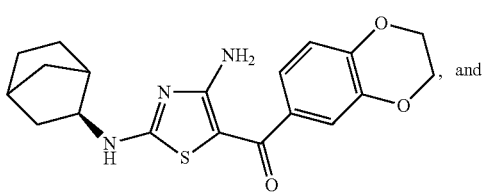, and

-continued

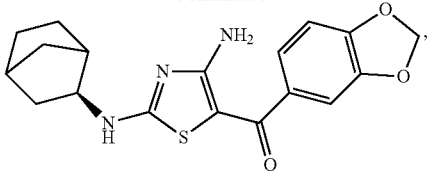

a salt or solvate thereof, and any combinations thereof.

Process

The present invention further relates to a process for preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art of organic chemistry. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions.

Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

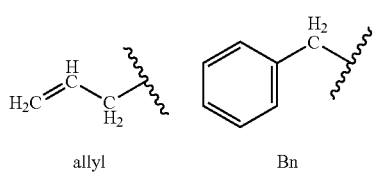

allyl          Bn

-continued

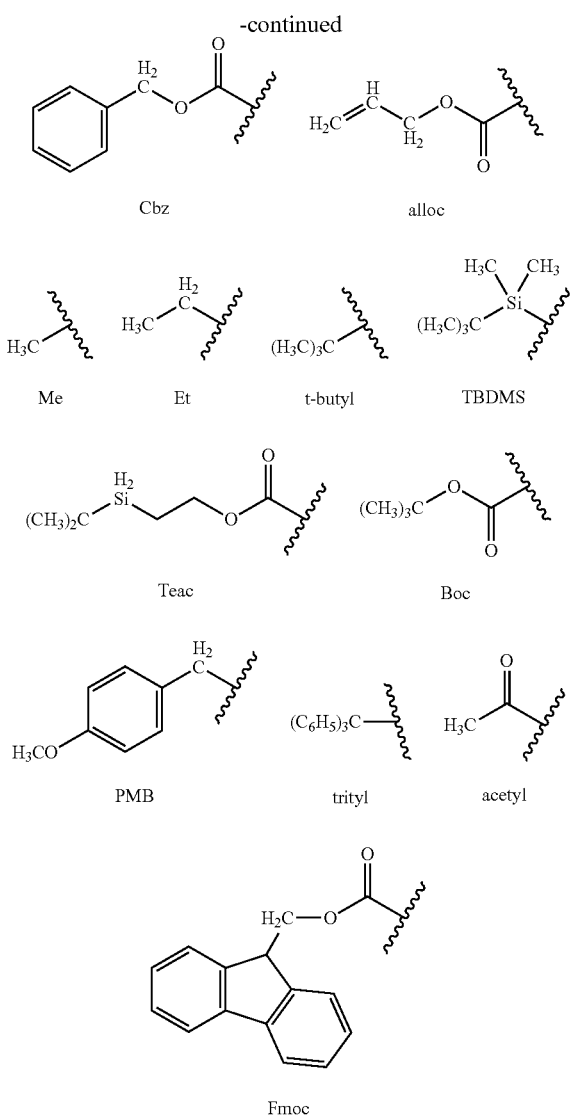

Cbz alloc

Me

Et t-butyl

TBDMS

Teac

Boc

PMB trityl acetyl

Fmoc

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

Exemplary General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Schemes 1-5.

Scheme 1

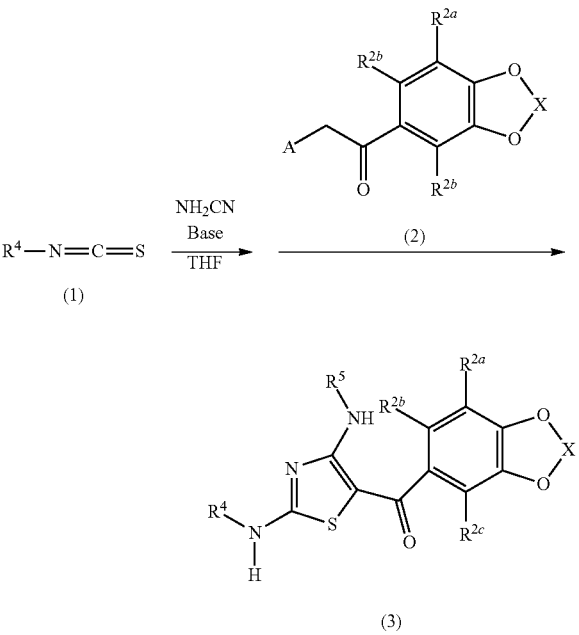

A compound of the formula (1), a known compound or a compound made by known methods, is reacted with cyanamide in the presence of a base such as potassium t-butoxide, sodium t-butoxide, lithium t-butoxide, sodium methoxide, sodium ethoxide, and the like in a solvent such as, N,N-dimethylformamide, 1,4-dioxane, tetrahydrofuran, methylene chloride and the like, optionally with heating, optionally with microwave irradiation. The resulting material is reacted with a compound of the formula (2), a known compound or a compound made by known methods wherein A is a leaving group such as bromine, chlorine, iodine, methansulfonate, p-tolulysaulfonate and the like, in the presence of a solvent such as N,N-dimethylformamide, 1,4-dioxane, tetrahydrofuran, methylene chloride and the like, optionally with heating, optionally with microwave irradiation to provide a compound of the formula (3).

Scheme 2

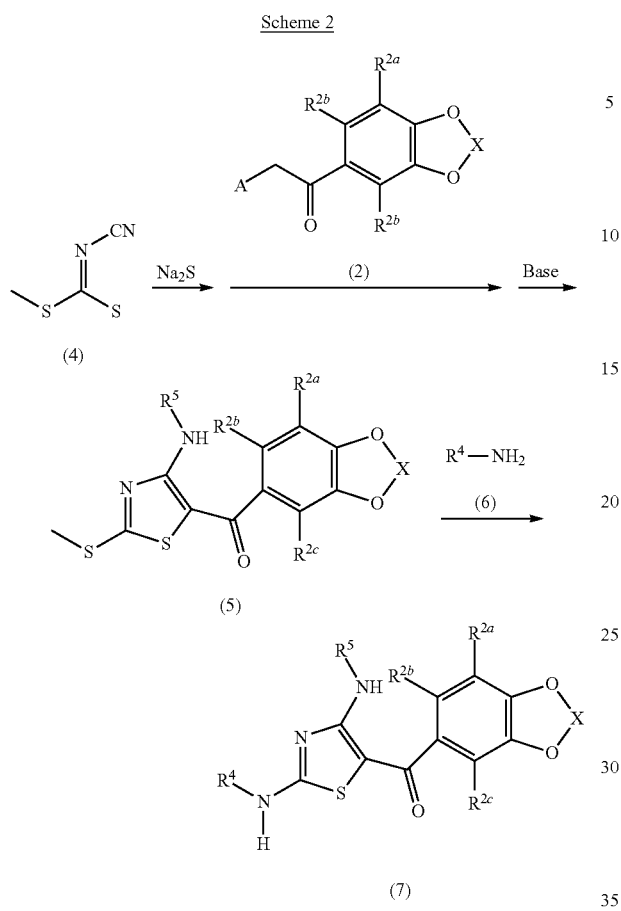

Scheme 3

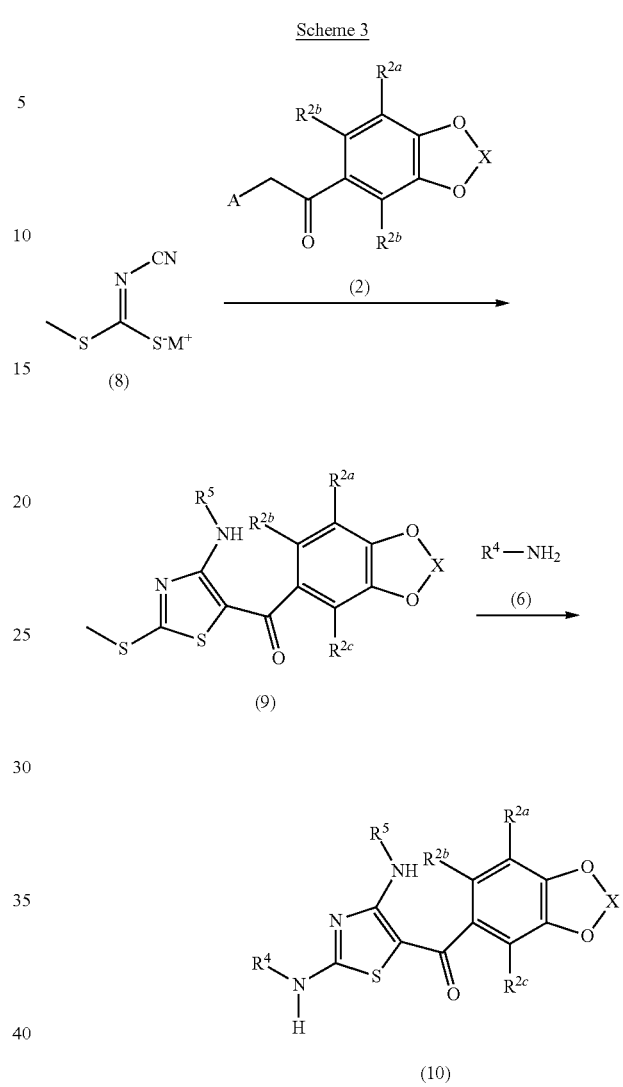

A compound of the formula (4) is reacted with sodium sulfide in the presence of a solvent such as N,N-dimethylformamide, N,N-dimethylacetamide, 1,4-dioxane, tetrahydrofuran, methylene chloride and the like, optionally with heating, optionally with microwave irradiation. The resulting material is reacted with a compound of the formula (2), a known compound or a compound made by known methods wherein A is a leaving group such as bromine, chlorine, iodine, methansulfonate, p-toluylsulfonate and the like, in the presence of a solvent such as N,N-dimethylformamide, 1,4-dioxane, tetrahydrofuran, methylene chloride and the like, optionally with heating, optionally with microwave irradiation. The resulting material is reacted with a base such as potassium carbonate, lithium carbonate, sodium carbonate, potassium hydroxide, lithium hydroxide, sodium hydroxide, and the like in the presence of a solvent such as N,N-dimethylformamide, 1,4-dioxane, tetrahydrofuran, methylene chloride and the like, optionally with heating, optionally with microwave irradiation to provide a compound of the formula (5). A compound of the formula (5) is reacted with a compounds of the formula (6), a known compound or a compound made by known methods, in the presence of a solvent such as ethanol, methanol, isopropanol, N,N-dimethylformamide, N,N-dimethylacetamide, 1,4-dioxane, tetrahydrofuran, methylene chloride and the like, optionally with heating, optionally with microwave irradiation to provide a compound of the formula (7).

A compound of the formula (8), a known compound or a compound made by known methods wherein M is a metal such as potassium, sodium, lithium and the like, is reacted with a compound of the formula (2) a known compound or a compound made by known methods, in the presence of a base such as triethylamine, diisopropylethylamine, N-methylmorpholine, pyridine and the like, in a solvent such as N,N-dimethylformamide, N,N-dimethylacetamide, 1,4-dioxane, tetrahydrofuran, methylene chloride and the like, optionally with heating, optionally with microwave irradiation to provide a compound of the formula (9). A compound of the formula (9) is reacted with a compound of the formula (6) a known compound or a compound made by known methods, in the presence of a solvent such as ethanol, methanol, isopropanol, N,N-dimethylformamide, N,N-dimethylacetamide, 1,4-dioxane, tetrahydrofuran, methylene chloride and the like, optionally with heating, optionally with microwave irradiation to provide a compound of the formula (10).

Scheme 4

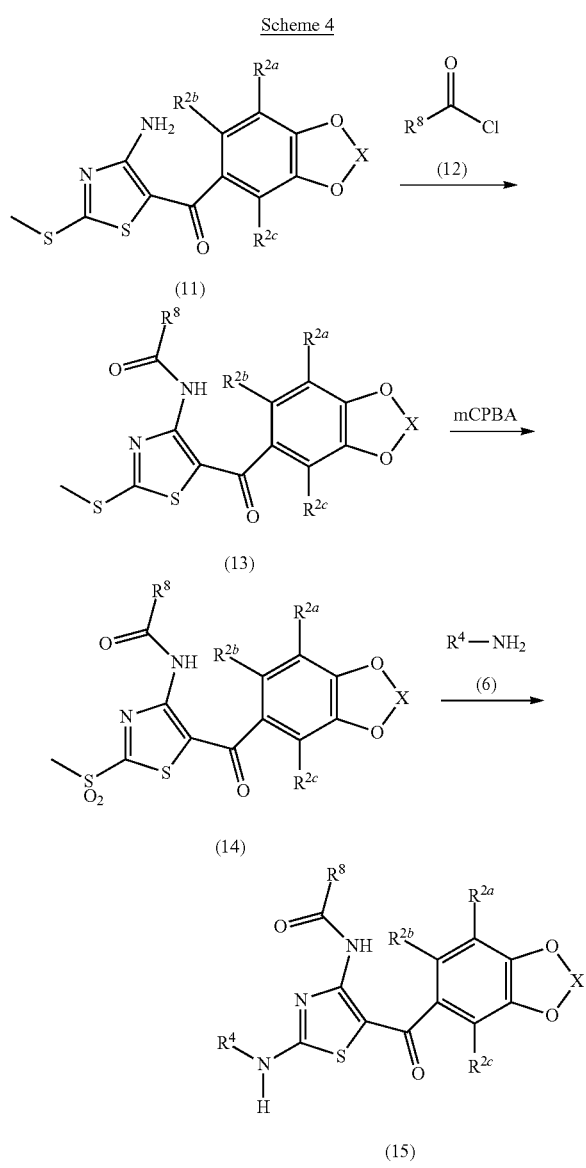

Scheme 5

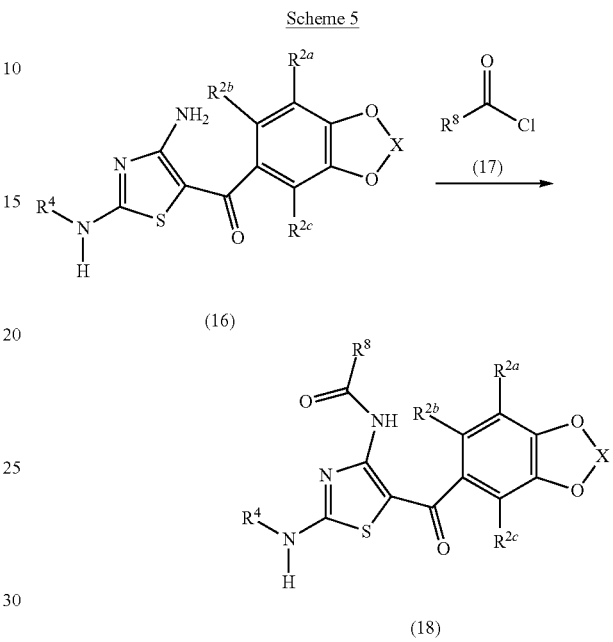

A compound of the formula (11), a known compound or a compound made by known methods, is reacted with a compound of the formula (12), a known compound or a compound made by known methods, in the presence of a base such as triethylamine, diisopropylethylamine, N-methylmorpholine, pyridine and the like, in a solvent such as acetonitrile, N,N-dimethylformamide, N,N-dimethylacetamide, 1,4-dioxane, tetrahydrofuran, methylene chloride and the like, optionally with heating, optionally with microwave irradiation to provide a compound of the formula (13). A compound of the formula (13) is reacted with meta-chloroperoxybenzoic acid (mCPBA) in the presence of a solvent such as acetonitrile, N,N-dimethylformamide, N,N-dimethylacetamide, 1,4-dioxane, tetrahydrofuran, methylene chloride and the like, optionally with heating, optionally with microwave irradiation to provide a compound of the formula (14). A compound of the formula (14) is reacted with a compound of the formula (6) a known compound or a compound made by known methods, optionally in the presence of a base such as triethylamine, diisopropylethylamine, N-methylmorpholine, pyridine and the like, in the presence of a solvent such as ethanol, methanol, isopropanol, N,N-dimethylformamide, N,N-dimethylacetamide, 1,4-dioxane, tetrahydrofuran, methylene chloride and the like, optionally with heating, optionally with microwave irradiation to provide a compound of the formula (15).

A compound of the formula (16) is reacted with a compound of the formula (17), a known compound or a compound made by known methods, in the presence of a base such as triethylamine, diisopropylethylamine, N-methylmorpholine, pyridine and the like, in a solvent such as acetonitrile, N,N-dimethylformamide, N,N-dimethylacetamide, 1,4-dioxane, tetrahydrofuran, methylene chloride and the like, optionally with heating, optionally with microwave irradiation to provide a compound of the formula (18).

Methods of the Invention

The invention includes a method of treating or preventing cancer in a subject in need thereof. The method comprises administering to the subject a therapeutically effective amount of a composition comprising a compound of the invention. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the compositions of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers that can be treated with the compositions of the invention include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, that can be treated with the compositions of the invention, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In one embodiment, the cancer is selected from the group consisting of lung cancer, colon cancer, melanoma, breast cancer, ovarian cancer, prostate cancer, liver cancer, pancreatic cancer, CNS tumors (including brain tumors), neuroblastoma, leukemia, bone cancer, intestinal cancer, lymphoma, and combinations thereof. In one embodiment, the cancer is breast cancer. In one embodiment, the method further comprises administering to the subject an additional therapeutic agent.

In one embodiment, administering the compound of the invention to the subject allows for administering a lower dose of the therapeutic agent compared to the dose of the therapeutic agent alone that is required to achieve similar results in treating or preventing cancer in the subject. For example, in one embodiment, the compound of the invention enhances the anti-cancer activity of the additional therapeutic compound, thereby allowing for a lower dose of the therapeutic compound to provide the same effect. In another embodiment, the compound of the invention enhances the anti-inflammatory activity of the additional therapeutic compound, thereby allowing for a lower dose of the therapeutic compound to provide the same effect. In another embodiment, the compound of the invention enhances the analgesic activity of the additional therapeutic compound, thereby allowing for a lower dose of the therapeutic compound to provide the same effect.

In one embodiment, the compound of the invention and the therapeutic agent are co-administered to the subject. In another embodiment, the compound of the invention and the therapeutic agent are coformulated and co-administered to the subject.

In one embodiment, the subject is a mammal. In another embodiment, the mammal is a human.

Therapies

The invention provides compositions and methods for treating cancer. In one embodiment, the invention provides a new class of compounds that have anti-cancer properties by targeting CDKs and reactivating silenced gene expression.

In one embodiment, the compounds of the invention can be used in combination with other epigenetic drugs to synergistically induce gene induction.

In one embodiment, the compounds to be useful in combination with one or more additional compounds. In certain embodiments, these additional compounds may comprise compounds of the present invention or therapeutic agents known to treat or reduce the symptoms or effects of cancer. Such compounds include, but are not limited to, chemotherapeutics and the like.

In non-limiting examples, the compounds of the invention may be used in combination with one or more therapeutic agents (or a salt, solvate or prodrug thereof).

The compounds of the invention can either be used alone or in combination with other anti-cancer drugs to treat cancer. One type of anti-cancer drug includes cytotoxic agents (i.e., drugs that kill cancer cells in different ways). These include the alkylating agents, antimetabolites, antitumor antibiotics, and plant drugs.

Another type of anti-cancer drug includes hormones and hormone antagonists. Some tumors require the presence of hormones to grow. Many of these drugs block the effects of hormones at its tissue receptors or prevent the manufacture of hormones by the body.

Another type of anti-cancer drug includes biological response modifiers. These drugs increase the body's immune system to detect and destroy the cancer.

Non-limiting examples of anti-cancer drugs include but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine;

mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfomithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; nemoronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

In certain embodiments, the compound of the invention may be administered to a subject in conjunction with (e.g. before, simultaneously, or following) any number of relevant treatment modalities including chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the compounds of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compounds of the present invention are administered following B-cell ablative therapy such as agents that react with CD20, e.g., Rituxan. In one embodiment, the additional therapeutic agent is Decitabine. In another embodiment, the additional therapeutic agent is an antimitotic agent. Non-limiting examples of antimitotic agents include paclitaxel, docetaxel, vinblastine, vincristine, topoisomerase inhibitors such as irenotecan, doxorubicin, and emcitabine.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either before or after the onset of cancer. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the cancer in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 μg to about 10,000 mg, from about 20 μg to about 9,500 mg, from about 40 μg to about 9,000 mg, from about 75 μg to about 8,500 mg, from about 150 μg to about 7,500 mg, from about 200 μg to about 7,000 mg, from about 3050 μg to about 6,000 mg, from about 500 μg to about 5,000 mg, from about 750 μg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties.

The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Application Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Synthesis of Aminothiazole Compounds

Synthesis of (4-amino-2-(propylamino)thiazol-5-yl)(2,3-dihydrobenzo[b][1,4]dioxin-6-yl)methanone (1)

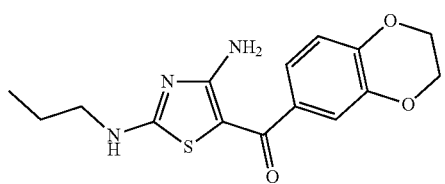 [SMILES: CCCNc1nc(N)c(C(=O)c2ccc3c(c2)OCCO3)s1]

Propyl isothiocyanate (0.2047 mmol; 21.2 µL) and solid potassium tert-butoxide (0.4504 mmol; 50.5 mg) were added sequentially to a solution of cyanamide (0.2047 mmol; 8.6 mg) in anhydrous tetrahydrofuran (1.0 mL). This mixture was stirred for 15 minutes. A solution of 2-bromo-1-(2,3-dihydro-1,4-benzodioxin-6-yl)ethan-1-one (0.1945 mmol; 50 mg) in anhydrous tetrahydrofuran (500 µL) was added. The resulting orange solution was stirred at room temperature overnight. It was concentrated down and the residue was partitioned between ethyl acetate and water. The aqueous layer was drained off. The organic layer was washed with brine, dried over anhydrous sodium sulfate and concentrated. The crude product was purified by column chromatography on silica gel using a gradient solvent system of 0 to 100% of ethyl acetate in hexanes to afford the titled compound as an orange-yellow glassy solid. $^1$H NMR (400 MHz, CD$_3$OD) δ 7.19 (m, 2H), 6.87 (m. 1H), 4.28 (m, 4H), 3.30 (m, 2H), 1.65 (m, 2H), 0.98 (t, J=7.40 Hz, 3H); ESIMS: m/z 320.1 [(M+H)$^+$].

Synthesis of (4-amino-2-(benzylamino)thiazol-5-yl)(2,3-dihydrobenzo[b][1,4]dioxin-6-yl)methanone (2)

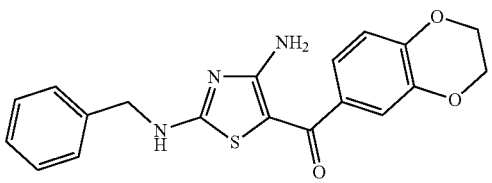 [SMILES: Nc1nc(NCc2ccccc2)sc1C(=O)c1ccc2c(c1)OCCO2]

Prepared using the same procedure as described for compound 1 substituting benzyl isothiocyanate in place of propyl isothiocyanate to afford compound 2 as an orange-yellow glassy solid. $^1$H NMR (400 MHz, CD$_3$OD) δ 7.34 (m, 4H), 7.28 (m, 1H), 7.18 (m, 2H), 6.86 (m, 1H), 4.55 (m, 2H), 4.27 (m, 4H); ESIMS: m/z 368.1 [(M+H)$^+$].

Synthesis of (4-amino-2-(methylamino)thiazol-5-yl)(2,3-dihydrobenzo[b][1,4]dioxin-6-yl)methanone (3)

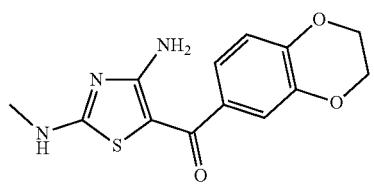 [SMILES: CNc1nc(N)c(C(=O)c2ccc3c(c2)OCCO3)s1]

Prepared using the same procedure as described for compound 1 substituting methyl isothiocyanate in place of propyl isothiocyanate to afford compound 3 as an orange-yellow oil. $^1$H NMR (400 MHz, CD$_3$OD) δ 7.19 (m, 2H), 6.87 (m, 1H), 4.28 (m, 4H), 2.94 (s, 3H); ESIMS: m/z 292.1 [(M+H)$^+$].

Synthesis of (4-amino-2-(isopropylamino)thiazol-5-yl)(2,3-dihydrobenzo[b][1,4]dioxin-6-yl)methanone (4)

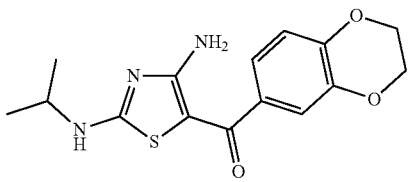 [SMILES: CC(C)Nc1nc(N)c(C(=O)c2ccc3c(c2)OCCO3)s1]

Prepared using the same procedure as described for compound 1 substituting isopropyl isothiocyanate in place of propyl isothiocyanate to afford compound 4 as a yellow solid. $^1$H NMR (400 MHz, CD$_3$OD) δ 7.18 (m, 1H), 6.86 (m, 1H), 4.27 (m, 4H), 3.30 (m, 1H), 1.25 (s, 3H), 1.24 (s, 3H); ESIMS: m/z 320.1 [(M+H)$^+$].

Synthesis of (4-amino-2-(butylamino)thiazol-5-yl)(2,3-dihydrobenzo[b][1,4]dioxin-6-yl)methanone (5)

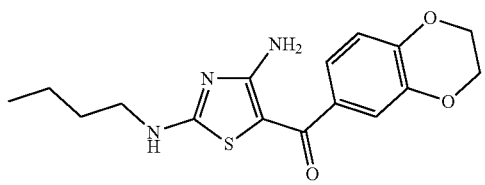 [SMILES: CCCCNc1nc(N)c(C(=O)c2ccc3c(c2)OCCO3)s1]

Prepared using the same procedure as described for compound 1 substitution butyl isothiocyanate in place of propyl isothiocyanate to afford compound 5 as a yellow solid. $^1$H NMR (400 MHz, CD$_3$OD) δ 7.18 (m, 2H), 6.86 (m, 1H), 4.27 (m, 4H), 3.30 (m, 2H), 1.60 (m, 2H), 1.40 (m, 2H), 0.96 (t, J=7.32 Hz, 3H); ESIMS: m/z 334.1 [(M+H)$^+$].

Synthesis of (4-amino-2-(ethylamino)thiazol-5-yl)(2,3-dihydrobenzo[b][1,4]dioxin-6-yl)methanone (6)

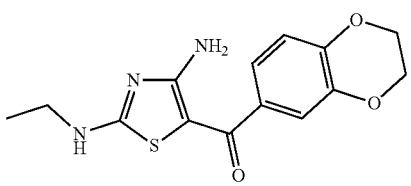 [SMILES: CCNc1nc(N)c(C(=O)c2ccc3c(c2)OCCO3)s1]

Prepared using the same procedure as described for compound 1 substituting ethyl isothiocyanate in place of propyl isothiocyanate to afford compound 6 as an orange-yellow oil. $^1$H NMR (400 MHz, CDCl$_3$) δ 7.31 (m, 2H), 6.88 (m, 1H), 4.29 (m, 4H), 3.30 (m, 2H), 1.29 (t, J=7.20 Hz, 3H); ESIMS: m/z 306.1 [(M+H)$^+$].

Synthesis of (4-amino-2-(cyclopentylamino)thiazol-5-yl)(2,3-dihydrobenzo[b][1,4]dioxin-6-yl)methanone (7)

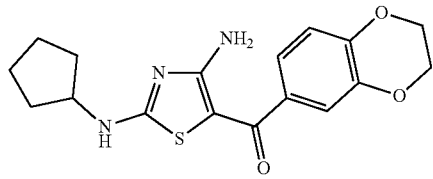 [SMILES: Nc1nc(NC2CCCC2)sc1C(=O)c1ccc2c(c1)OCCO2]

Prepared using the same procedure as described for compound 1 substituting cyclopentyl isothiocyanate in place of propyl isothiocyanate to afford compound 7 as an orange-yellow oil. $^1$H NMR (400 MHz, CDCl$_3$) δ 7.31 (m, 2H), 6.88 (d, J=8.28 Hz, 1H), 5.67 (m, 1H), 4.29 (m, 4H), 3.80 (m, 1H), 2.04 (m, 2H), 1.50-1.80 (m, 6H); ESIMS: m/z 346.1 [(M+H)$^+$].

Synthesis of (4-amino-2-(cyclohexylamino)thiazol-5-yl)(2,3-dihydrobenzo[b][1,4]dioxin-6-yl)methanone (8)

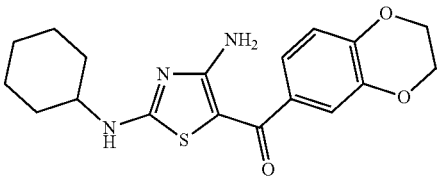 [SMILES: Nc1nc(NC2CCCCC2)sc1C(=O)c1ccc2c(c1)OCCO2]

Prepared using the same procedure as described for compound 1 substituting cyclohexyl isothiocyanate in place of propyl isothiocyanate to afford compound 8 as an orange-yellow glassy solid. $^1$H NMR (400 MHz, CDCl$_3$) δ 7.30 (m, 2H), 6.88 (d, J=8.28 Hz, 1H), 5.62 (m, 1H), 4.29 (m, 4H), 3.30 (m, 1H), 2.04 (m, 2H), 1.78 (M, 2H), 1.20-1.42 (m, 6H); ESIMS: m/z 360.1 [(M+H)$^+$].

Synthesis of (4-amino-2-((4-methoxybenzyl)amino)thiazol-5-yl)(2,3-dihydrobenzo[b][1,4]dioxin-6-yl)methanone (9)

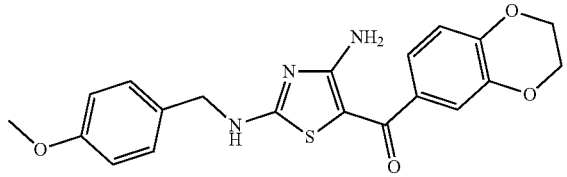 [SMILES: COc1ccc(CNc2nc(N)c(C(=O)c3ccc4c(c3)OCCO4)s2)cc1]

Prepared using the same procedure as described for compound 1 to substituting 4-methoxybenzyl isothiocyanate in place of propyl isothiocyanate afford compound 9 as an orange-yellow glassy solid. $^1$H NMR (400 MHz, CDCl$_3$) δ 7.23-7.32 (m, 4H), 6.88 (m, 3H), 6.35 (bs, 1H), 4.39 (m, 2H), 4.28 (m, 4H), 3.80 (s, 3H); ESIMS: m/z 398.1 [(M+H)$^+$].

Synthesis of (4-amino-2-((methoxymethyl)amino)thiazol-5-yl)(2,3-dihydrobenzo[b][1,4]dioxin-6-yl)methanone (10)

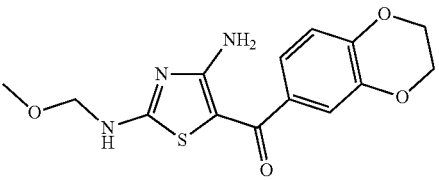 [SMILES: COCNc1nc(N)c(C(=O)c2ccc3c(c2)OCCO3)s1]

Prepared using the same procedure as described for compound 1 substituting methoxymethyl isothiocyanate in place of propyl isothiocyanate to afford compound 10 as an orange-yellow glassy solid. $^1$H NMR (400 MHz, CDCl$_3$) δ 7.30 (m, 2H), 6.88 (d, J=8.28 Hz, 1H), 6.70 (bs, 1H), 4.29 (m, 4H), 3.37 (s, 3H); ESIMS: m/z 322.0 [(M+H)$^+$].

Synthesis of (4-amino-2-(phenethylamino)thiazol-5-yl)(2,3-dihydrobenzo[b][1,4]dioxin-6-yl)methanone (11)

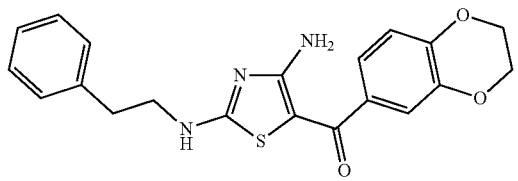 [SMILES: Nc1nc(NCCc2ccccc2)sc1C(=O)c1ccc2c(c1)OCCO2]

Prepared using the same procedure as described for compound 1 substituting 2-phenylethyl isothiocyanate in place of propyl isothiocyanate to afford compound 11 as an orange-yellow glassy solid. $^1$H NMR (400 MHz, CDCl$_3$) δ 7.27-7.35 (m, 5H), 7.19 (m, 2H), 6.88 (d, J=8.28 Hz, 1H), 5.72 (bs, 1H), 4.29 (m, 4H), 3.53 (m, 2H), 2.94 (t, J=6.80 Hz, 2H); ESIMS: m/z 382.1 [(M+H)$^+$].

Synthesis of (4-amino-2-((4-methoxyphenethyl)amino)thiazol-5-yl)(2,3-dihydrobenzo[b][1,4]dioxin-6-yl)methanone (12)

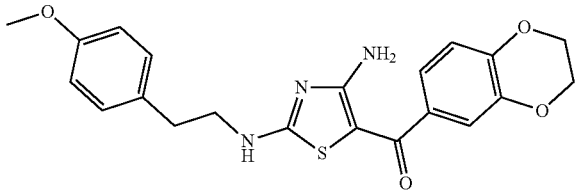 [SMILES: COc1ccc(CCNc2nc(N)c(C(=O)c3ccc4c(c3)OCCO4)s2)cc1]

Prepared using the same procedure as described for compound 1 substituting 1-(2-isothiocyanatoethyl)-4-methoxybenzene in place of propyl isothiocyanate to afford compound 12 as an orange-yellow solid. $^1$H NMR (400 MHz, CDCl$_3$) δ 7.30 (m, 2H), 7.11 (M, 2H), 6.87 (M, 3H), 5.64 (bs, 1H), 4.29 (m, 4H), 3.80 (s, 3H), 3.49 (m, 2H), 2.88 (t, J=6.80 Hz, 2H); ESIMS: m/z 412.1 [(M+H)$^+$].

Synthesis of (4-amino-2-((1-phenylethyl)amino)thiazol-5-yl)(2,3-dihydrobenzo[b][1,4]dioxin-6-yl)methanone (13)

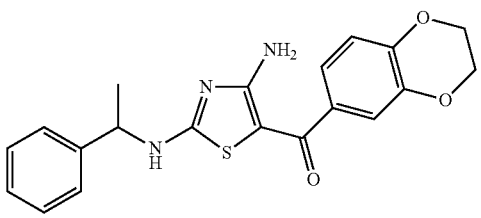 [SMILES: CC(Nc1nc(N)c(C(=O)c2ccc3c(c2)OCCO3)s1)c1ccccc1]

Prepared using the same procedure as described for compound 1 substituting 1-phenylethyl isothiocyanate in place of propyl isothiocyanate to afford compound 13 as an orange-yellow solid. $^1$H NMR (400 MHz, CDCl$_3$) δ 7.22-7.37 (m, 7H), 6.85 (d, J=8.32 Hz, 1H), 6.11 (m, 1H), 4.66 (m 1H), 4.27 (m, 4H), 1.60 (d, J=6.76 Hz, 3H); ESIMS: m/z 382.1 [(M+H)$^+$].

Synthesis of (R)-(4-amino-2-((1-(4-methoxyphenyl)ethyl)amino)thiazol-5-yl)(2,3-dihydrobenzo[b][1,4]dioxin-6-yl)methanone (14)

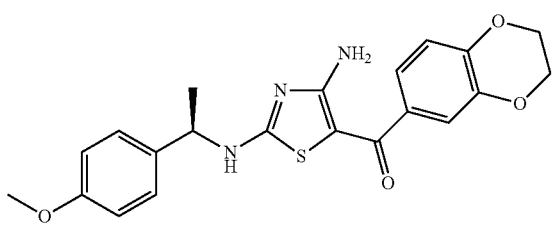 [SMILES: COc1ccc([C@@H](C)Nc2nc(N)c(C(=O)c3ccc4c(c3)OCCO4)s2)cc1]

Prepared using the same procedure as described for compound 1 substituting (R)-1-(4-methoxyphenyl)ethyl isothiocyanate in place of propyl isothiocyanate to afford compound 14 as an orange-yellow glassy solid. $^1$H NMR (400 MHz, CDCl$_3$) δ 7.25 (m, 4H), 6.86 (m, 3H), 6.02 (M, 1H), 4.60 (m, 1H), 4.28 (m, 4H), 3.80 (s, 3H), 1.57 (d, J=6.76 Hz, 3H); ESIMS: m/z 412.1 [(M+H)$^+$].

Synthesis of (S)-(4-amino-2-((2,3-dihydro-1H-inden-1-yl)amino)thiazol-5-yl)(2,3-dihydrobenzo[b][1,4]dioxin-6-yl)methanone (15)

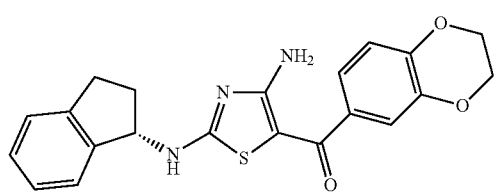 [SMILES: Nc1nc(N[C@H]2CCc3ccccc32)sc1C(=O)c1ccc2c(c1)OCCO2]

Prepared using the same procedure as described for compound 1 substituting (S)-1-indanyl isothiocyanate in place of propyl isothiocyanate to afford compound 15 as an orange-yellow glassy solid. $^1$H NMR (400 MHz, CDCl$_3$) δ 7.39 (bd, J=7.32 Hz, 1H), 7.24-7.32 (m, 5H), 6.87 (d, J=8.32 Hz, 1H), 5.01 (m, 1H), 4.28 (m, 4H), 3.03 (M, 1H), 2.89 (m, 1H), 2.69 (m, 1H), 1.93 (m, 1H); ESIMS: m/z 394.1 [(M+H)$^+$].

Synthesis of (4-amino-2-(methylthio)thiazol-5-yl)(2,3-dihydrobenzo[b][1,4]dioxin-6-yl)methanone (16)

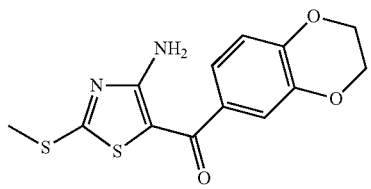 [SMILES: CSc1nc(N)c(C(=O)c2ccc3c(c2)OCCO3)s1]

2-bromo-1-(2,3-dihydro-1,4-benzodioxin-6-yl)ethan-1-one (0.3890 mmol; 100 mg) and triethylamine (0.5018 mmol; 70 uL) were added sequentially to a solution of cyanimidodithiocarbonic acid S-methyl ester S-potassium salt (0.3493 mmol; 59.5 mg) in anhydrous dimethylformamide (2.0 mL). This mixture was stirred at 80° C. for 3 hours. It was cooled to room temperature and concentrated down. The residue was partitioned between ethyl acetate and water. The aqueous layer was drained off. The organic layer was washed with brine, dried over anhydrous sodium sulfate and concentrated. The crude product was purified by column chromatography on silica gel using a gradient solvent system of 0 to 100% of ethyl acetate in hexanes to afford compound 16 as a yellow solid. $^1$H NMR (400 MHz, CDCl$_3$) δ 7.33 (m, 2H), 6.90 (d, J=8.28 Hz, 1H), 4.30 (m, 4H), 2.66 (s, 3H); ESIMS: m/z 309.1 [(M+H)$^+$].

Synthesis of (4-amino-2-((2S)-bicyclo[2.2.1]heptan-2-ylamino)thiazol-5-yl)(2,3-dihydrobenzo[b][1,4]dioxin-6-yl)methanone (17)

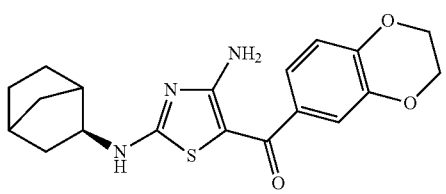 [SMILES: Nc1nc(N[C@H]2CC3CCC2C3)sc1C(=O)c1ccc2c(c1)OCCO2]

A solution of (4-amino-2-(methylthio)thiazol-5-yl)(2,3-dihydrobenzo[b][1,4]dioxin-6-yl)methanone (0.0649 mmol; 20 mg) and exo-2-aminonorbornane (1.298 mmol; 154 uL) in ethanol (500 uL) was stirred at 100° C. in a glass pressure vessel overnight. The solution was cooled to room temperature and concentrated down. The crude product was purified by column chromatography on silica gel using a gradient solvent system of 0 to 100% of ethyl acetate in hexanes to afford compound 17 as a yellow solid. $^1$H NMR (400 MHz, CDCl$_3$) δ 7.31 (m, 2H), 6.89 (d, J=8.24 Hz, 1H), 5.52 (d, J=7.32 Hz, 1H), 4.29 (m, 4H), 3.27 (m, 2H), 2.35 (m, 2H), 1.89 (m, 1H), 1.62-1.45 (m, 3H), 1.38 (m, 1H), 1.12-1.32 (m, 4H); ESIMS: m/z 372.1 [(M+H)$^+$].

Synthesis of (4-amino-2-((tetrahydro-2H-pyran-4-yl)amino)thiazol-5-yl)(2,3-dihydrobenzo[b][1,4]dioxin-6-yl)methanone (18)

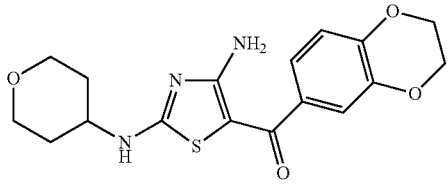 [SMILES: Nc1nc(NC2CCOCC2)sc1C(=O)c1ccc2c(c1)OCCO2]

Prepared using the same procedure as described for compound 17 substituting 4-aminopyran in place of exo-2-aminonorbornane to afford compound 18 as an orange-yellow solid. $^1$H NMR (400 MHz, CDCl$_3$) δ 7.30 (m, 2H), 6.89 (d, J=8.28 Hz, 1H), 5.43 (m, 1H), 4.29 (m, 4H), 3.99 (m, 2H), 3.62 (m, 1H), 3.49 (m, 2H), 2.06 (m, 2H), 1.58 (m, 2H); ESIMS: m/z 362.1 [(M+H)$^+$].

Synthesis of (4-amino-2-((3-methoxycyclopentyl)amino)thiazol-5-yl)(2,3-dihydrobenzo[b][1,4]dioxin-6-yl)methanone (19)

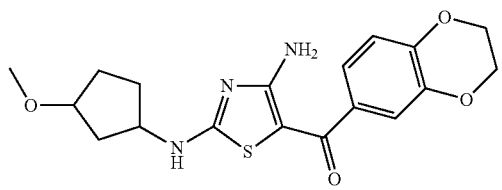 [SMILES: COC1CCC(Nc2nc(N)c(C(=O)c3ccc4c(c3)OCCO4)s2)C1]

Prepared using the same procedure as described for compound 17 substituting 3-methoxycyclopentyl amine in place of exo-2-aminonorbornane to afford compound 19 as an orange-yellow glassy solid. $^1$H NMR (400 MHz, CDCl$_3$) δ 7.31 (m, 2H), 6.89 (m, 1H), 5.64 (m, 1H), 4.29 (m, 4H), 3.97 (m, 1H), 3.91 (m, 1H), 3.28 (d, J=3.80 Hz, 3H), 2.26 (m, 1H), 1.48-1.99 (m, 5H); ESIMS: m/z 376.2 [(M+H)$^+$].

Synthesis of (4-amino-2-(isobutylamino)thiazol-5-yl)(2,3-dihydrobenzo[b][1,4]dioxin-6-yl)methanone (20)

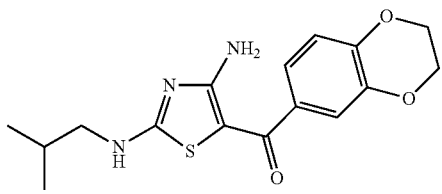 [SMILES: CC(C)CNc1nc(N)c(C(=O)c2ccc3c(c2)OCCO3)s1]

Prepared using the same procedure as described for compound 17 substituting isobutylamine in place of exo-2-aminonorbornane to afford compound 20 as a yellow solid. $^1$H NMR (400 MHz, CDCl$_3$) δ 7.30 (m, 2H), 6.88 (d, J=8.28 Hz, 1H), 5.69 (m, 1H), 4.29 (m, 4H), 3.07 (t, J=6.40 Hz, 2H), 1.93 (m, 1H), 0.97 (d, J=6.68 Hz, 6H); ESIMS: m/z 689.3 [(2M+Na)$^+$].

Synthesis of (4-amino-2-(cyclopropylamino)thiazol-5-yl)(2,3-dihydrobenzo[b][1,4]dioxin-6-yl)methanone (21)

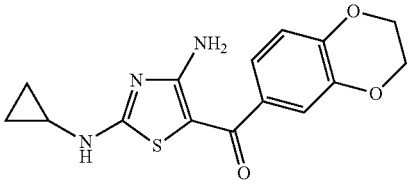 [SMILES: Nc1nc(NC2CC2)sc1C(=O)c1ccc2c(c1)OCCO2]

Prepared using the same procedure as described for compound 17 substituting cyclopropylamine in place of exo-2-aminonorbornane to afford compound 21 as an orange-yellow glassy solid. $^1$H NMR (400 MHz, CDCl$_3$) δ 7.33 (m, 2H), 6.90 (d, J=8.24 Hz, 1H), 6.30 (bs, 1H), 4.29 (m, 4H), 2.60 (m, 1H), 0.84 (m, 2H), 0.71 (m, 2H); ESIMS: m/z 657.2 [(2M+Na)$^+$].

Synthesis of (4-amino-2-((1-methylpiperidin-4-yl)amino)thiazol-5-yl)(2,3-dihydrobenzo[b][1,4]dioxin-6-yl)methanone (22)

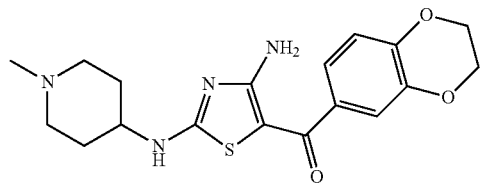 [SMILES: CN1CCC(Nc2nc(N)c(C(=O)c3ccc4c(c3)OCCO4)s2)CC1]

Prepared using the same procedure as described for compound 17 substituting 1-methyl-4-aminopiperidine in place of exo-2-aminonorbornane to afford compound 22 an orange-yellow glassy solid. $^1$H NMR (400 MHz, CD$_3$OD) δ 7.17 (m, 2H), 6.87 (m, 1H), 4.28 (m, 4H), 3.98 (m, 1H), 3.58 (m, 2H), 3.14 (m, 2H), 2.89 (s, 3H), 2.36 (m, 2H), 1.76 (m, 2H); ESIMS: m/z 771.3 [(2M+Na)$^+$].

Synthesis of (4-amino-2-((furan-2-ylmethyl)amino)thiazol-5-yl)(2,3-dihydrobenzo[b][1,4]dioxin-6-yl)methanone (23)

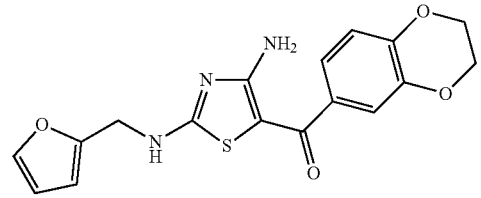 [SMILES: Nc1nc(NCc2ccco2)sc1C(=O)c1ccc2c(c1)OCCO2]

Prepared using the same procedure as described for compound 17 substituting 2-aminomethylfuran in place of exo-2-aminonorbornane to afford compound 23 as a reddish-tan solid. $^1$H NMR (400 MHz, CDCl$_3$) δ 7.39 (m, 1H), 7.30 (m, 2H), 6.88 (d, J=8.32 Hz, 1H), 6.34 (m, 2H), 6.07 (m, 1H), 4.47 (m, 2H), 4.29 (m, 4H); ESIMS: m/z 737.2 [(2M+Na)$^+$].

Synthesis of (2-(adamantan-2-ylamino)-4-aminothiazol-5-yl)(2,3-dihydrobenzo[b][1,4]dioxin-6-yl)methanone (24)

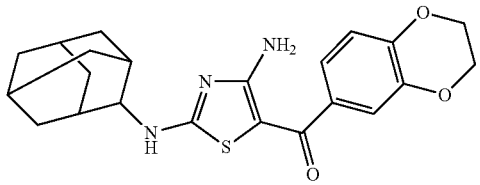 [SMILES: Nc1nc(NC2C3CC4CC(C3)CC2C4)sc1C(=O)c1ccc2c(c1)OCCO2]

Prepared using the same procedure as described for compound 17 substituting 2-aminoadamantane in place of exo-2-aminonorbornane to afford compound 24 as an off-white solid. $^1$H NMR (400 MHz, CDCl$_3$) δ 7.30 (m, 2H), 6.89 (d, J=8.24 Hz, 1H), 5.97 (m, 1H), 4.29 (m, 4H), 3.55 (m, 1H), 2.08 (bs, 2H), 1.66-1.92 (m, 12H); ESIMS: m/z 412.1 [(M+H)$^+$].

Synthesis of N-(2-(cyclopentylamino)-5-(2,3-dihydrobenzo[b][1,4]dioxine-6-carbonyl)thiazol-4-yl)acetamide (25)

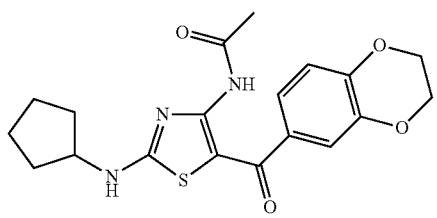 [SMILES: CC(=O)Nc1nc(NC2CCCC2)sc1C(=O)c1ccc2c(c1)OCCO2]

Step 1: Synthesis of N-(5-(2,3-dihydrobenzo[b][1,4]dioxine-6-carbonyl)-2-(methylthio)thiazol-4-yl)acetamide (31)

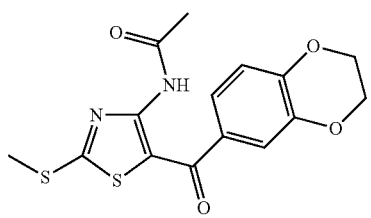 [SMILES: CSc1nc(NC(C)=O)c(C(=O)c2ccc3c(c2)OCCO3)s1]

Pyridine (0.4865 mmol; 39 μL) and acetyl chloride (0.4865 mmol; 35 μL) were added sequentially to a solution of (4-amino-2-(methylthio)thiazol-5-yl)(2,3-dihydrobenzo[b][1,4]dioxin-6-yl)methanone (0.3243 mmol; 100 mg) in anhydrous dichloromethane (2.0 mL). The resulting clear orange solution was stirred at room temperature overnight. The solution was concentrated down and the residue was partitioned between ethyl acetate and water. The aqueous layer was drained off. The organic layer was washed with brine, dried over anhydrous sodium sulfate and concentrated. The crude product was purified by column chromatography on silica gel using a gradient solvent system of 0 to 100% of ethyl acetate in hexanes to afford compound 31 as an orange-yellow solid. $^1$H NMR (400 MHz, CDCl$_3$) δ 11.06 (s, 1H), 7.35 (m, 2H), 6.93 (d, J=8.24 Hz, 1H), 4.32 (m, 4H), 2.74 (s, 3H), 2.43 (s, 3H); ESIMS: m/z 723.1 [(2M+Na)$^+$].

Step 2: Synthesis of N-(5-(2,3-dihydrobenzo[b][1,4]dioxine-6-carbonyl)-2-(methylsulfonyl)thiazol-4-yl)acetamide (32)

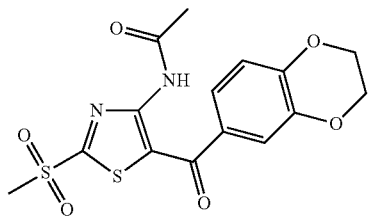 [SMILES: CC(=O)Nc1nc(S(C)(=O)=O)sc1C(=O)c1ccc2c(c1)OCCO2]

m-Chloroperbenzoic acid (0.4353 mmol, 107 mg of 70% purity) was added to a solution of N-(5-(2,3-dihydrobenzo[b][1,4]dioxine-6-carbonyl)-2-(methylthio)thiazol-4-yl)acetamide (compound 26) (0.1741 mmol; 61 mg) in anhydrous dichloromethane (2 mL) and stirred at room temperature overnight. The solution was concentrated down. The residue was dissolved into ethyl acetate, washed with saturated aqueous sodium bicarbonate solution, dried over anhydrous sodium sulfate and concentrated to afford compound 32 as a yellow solid. $^1$H NMR (400 MHz, CDCl$_3$) δ 10.46 (s, 1H), 7.41 (m, 2H), 6.98 (m, 1H), 4.34 (m, 4H), 3.40 (s, 3H), 2.40 (s, 3H); ESIMS: m/z 787.0 [(2M+Na)$^+$].

Step 3: Synthesis of N-(2-(cyclopentylamino)-5-(2,3-dihydrobenzo[b][1,4]dioxine-6-carbonyl)thiazol-4-yl)acetamide (25)

Cyclopentylamine (0.1046 mmol; 10.3 μL) and trimethylamine (0.1396 mmol; 19.5 μL) were added sequentially to a solution of N-(5-(2,3-dihydrobenzo[b][1,4]dioxine-6-carbonyl)-2-(methylsulfonyl)thiazol-4-yl)acetamide (compound 32) (0.0523 mmol; 20 mg) in anhydrous dioxane (2 mL). This solution was stirred at room temperature overnight and then concentrated down. The crude product was purified by column chromatography on silica gel using a gradient solvent system of 0 to 100% of ethyl acetate in hexanes to afford the titled compound as an orange-yellow glassy solid. $^1$H NMR (400 MHz, CDCl$_3$) δ 11.83 (s, 1H), 7.33 (m, 2H), 6.92 (d, J=8.24 Hz, 1H), 6.27 (bs, 1H), 4.31 (m, 4H), 3.74 (m, 1H), 2.31 (s, 3H), 2.04 (m, 2H), 1.56-1.78 (m, 6H); ESIMS: m/z 388.1 [(M+H)$^+$].

Synthesis of tert-butyl (2-((2S)-bicyclo[2.2.1]heptan-2-ylamino)-5-(2,3-dihydrobenzo[b][1,4]dioxine-6-carbonyl)thiazol-4-yl)carbamate (26)

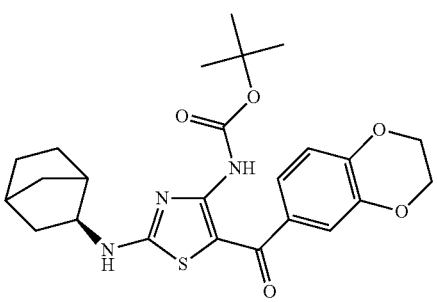 [SMILES: CC(C)(C)OC(=O)Nc1nc(N[C@H]2CC3CCC2C3)sc1C(=O)c1ccc2c(c1)OCCO2]

Step 1: Synthesis of tert-butyl (5-(2,3-dihydrobenzo[b][1,4]dioxine-6-carbonyl)-2-(methylthio)thiazol-4-yl)carbamate (33)

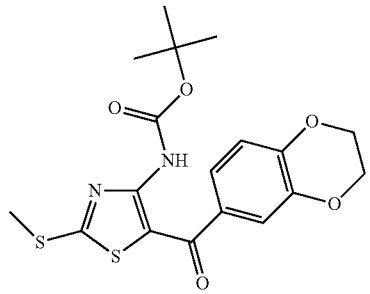 [SMILES: CSc1nc(NC(=O)OC(C)(C)C)c(C(=O)c2ccc3c(c2)OCCO3)s1]

(4-amino-2-(methylthio)thiazol-5-yl)(2,3-dihydrobenzo[b][1,4]dioxin-6-yl)methanone (1.621 mmol; 500 mg) was suspended in anhydrous dichloromethane (10 mL). A solution of di-tert-butyl dicarbonate (1.783 mmol; 389 mg) in anhydrous dichloromethane (10 mL) was added followed by dimethylaminopyridine (0.162 mmol; 20 mg). The resulting orange solution was stirred at room temperature under argon for 20 hours. The solution was concentrated down. The crude product was purified by column chromatography on silica gel using a gradient solvent system of 0 to 10% of ethyl acetate in dichloromethane to afford compound 33 as a light yellow foamy solid. $^1$H NMR (400 MHz, CDCl$_3$) δ 10.59 (s, 1H), 7.36 (m, 1H), 7.33 (m, 1H), 6.93 (M, 1H), 4.31 (m, 4H), 2.73 (s, 3H), 1.54 (s, 9H); ESIMS: m/z 839.1 [(2M+Na)$^+$].

Step 2: Synthesis of tert-butyl (5-(2,3-dihydrobenzo[b][1,4]dioxine-6-carbonyl)-2-(methylsulfonyl)thiazol-4-yl)carbamate (34)

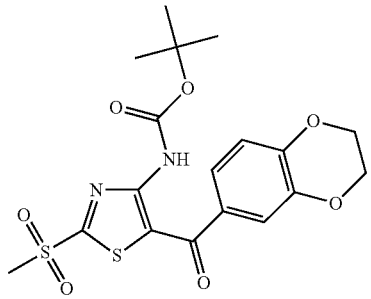 [SMILES: CC(C)(C)OC(=O)Nc1nc(S(C)(=O)=O)sc1C(=O)c1ccc2c(c1)OCCO2]

Prepared from compound 33 using the same procedure as described for compound 32 to afford compound 34 as a crystalline yellow solid. $^1$H NMR (400 MHz, CDCl$_3$) δ 9.96 (s, 1H), 7.40 (m, 2H), 6.97 (m, 1H), 4.32 (m, 4H), 3.41 (s, 3H), 1.53 (s, 9H); ESIMS: m/z 903.1 [(2M+Na)$^+$].

Step 3: Synthesis of tert-butyl (2-(((2S)-bicyclo[2.2.1]heptan-2-ylamino)-5-(2,3-dihydrobenzo[b][1,4]dioxine-6-carbonyl)thiazol-4-yl)carbamate (26)

Prepared from compound 34 using the same procedure as described for compound 25 to afford compound 26 as a yellow glassy solid. $^1$H NMR (400 MHz, CDCl$_3$) δ 11.16 (s, 1H), 7.33 (m, 2H), 6.92 (m, 1H), 6.12 (m, 1H), 4.30 (m, 4H), 3.18 (m, 1H), 2.34 (m, 2H), 1.89 (m, 1H), 1.53 (m, 10H), 1.12-1.40 (m, 6H); ESIMS: m/z 472.2 [(M+H)$^+$].

Synthesis of N-(2-(((2S)-bicyclo[2.2.1]heptan-2-ylamino)-5-(2,3-dihydrobenzo[b][1,4]dioxine-6-carbonyl)thiazol-4-yl)butyramide (27)

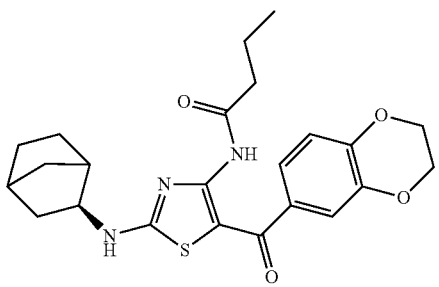 [SMILES: CCCC(=O)Nc1nc(N[C@H]2CC3CCC2C3)sc1C(=O)c1ccc2c(c1)OCCO2]

Butyryl chloride (0.0620 mmol; 6.4 uL) was added to a solution of compound 17 (4-amino-2-((2S)-bicyclo[2.2.1]heptan-2-ylamino)thiazol-5-yl)(2,3-dihydrobenzo[b][1,4]dioxin-6-yl)methanone (0.0385 mmol; 14.3 mg) and pyridine (0.0578 mmol; 4.7 μL) in anhydrous dichloromethane (500 μL). This solution was stirred at room temperature for 1 hour and then concentrated down. The crude product was purified by column chromatography on silica gel using a gradient solvent system of 0 to 100% of ethyl acetate in hexanes to afford the titled compound as a yellow glassy solid. $^1$H NMR (400 MHz, CDCl$_3$) δ 11.87 (s, 1H), 7.33 (m, 2H), 6.92 (m, 1H), 6.27 (bs, 1H), 4.31 (m, 4H), 3.20 (m, 1H), 2.48 (m, 2H), 2.34 (m, 2H), 1.12-1.93 (m, 13H); ESIMS: m/z 442.1 [(M+H)$^+$].

Synthesis of N-(2-(((2S)-bicyclo[2.2.1]heptan-2-ylamino)-5-(2,3-dihydrobenzo[b][1,4]dioxine-6-carbonyl)thiazol-4-yl)acetamide (28)

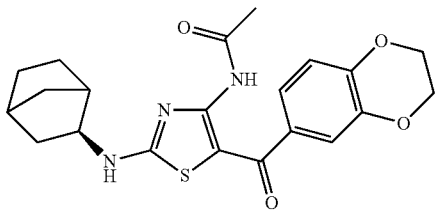 [SMILES: CC(=O)Nc1nc(N[C@H]2CC3CCC2C3)sc1C(=O)c1ccc2c(c1)OCCO2]

Prepared using the same procedure as described for compound 25 from compound 32 and exo-1-aminonorbomane to afford compound 28 as a yellow glassy solid. $^1$H NMR (400 MHz, CDCl$_3$) δ 11.83 (s, 1H) 7.32 (m, 2H), 6.93 (m, 1H), 6.19 (bs, 1H), 4.31 (m, 4H), 3.21 (m, 1H), 2.36 (m, 2H), 2.31 (s, 3H), 1.89 (m, 1H), 1.10-1.65 (m, 7H); ESIMS: m/z 414.1 [(M+H)$^+$].

Synthesis of (4-amino-2-((2S)-bicyclo[2.2.1]heptan-2-ylamino)thiazol-5-yl)(3,4-dihydro-2H-benzo[b][1,4]dioxepin-7-yl)methanone (29)

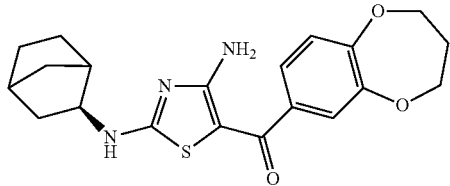 [SMILES: Nc1nc(N[C@H]2CC3CCC2C3)sc1C(=O)c1ccc2c(c1)OCCCO2]

Step 1: Synthesis of (4-amino-2-(methylthio)thiazol-5-yl)(3,4-dihydro-2H-benzo[b][1,4]dioxepin-7-yl)methanone (35)

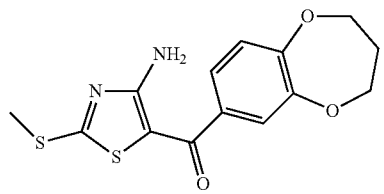 [SMILES: CSc1nc(N)c(C(=O)c2ccc3c(c2)OCCCO3)s1]

Prepared using the same procedure as described for compound 16 substituting 7-bromo-3,4-dihydro-1,5-benzodioxepine in place of 2-bromo-1-(2,3-dihydro-1,4-benzodioxin-6-yl)ethan-1-one to afford compound 35 as an orange solid. $^1$H NMR (400 MHz, CDCl$_3$) δ 7.39 (m, 2H), 6.99 (m, 1H), 4.28 (m, 4H), 2.65 (s, 3H), 2.22 (m, 2H); ESIMS: m/z 323.0 [(M+H)$^+$].

Step 2: Synthesis of (4-amino-2-((2S)-bicyclo[2.2.1]heptan-2-ylamino)thiazol-5-yl)(3,4-dihydro-2H-benzo[b][1,4]dioxepin-7-yl)methanone (29)

Prepared from compound 35 using the same procedure as described for compound 17 to afford compound 24 as an orange-yellow glassy solid. $^1$H NMR (400 MHz, CD$_3$OD) δ 7.26 (m, 2H); 6.97 (m, 1H), 4.22 (m, 4H), 2.32 (m, 2H), 2.19 (m, 2H), 1.81 (m, 1H), 1.14-1.61 (m, 8H); ESIMS: m/z 386.1 [(M+H)$^+$].

Synthesis of (4-amino-2-((2S)-bicyclo[2.2.1]heptan-2-ylamino)thiazol-5-yl)(benzo[d][1,3]dioxol-5-yl)methanone (30)

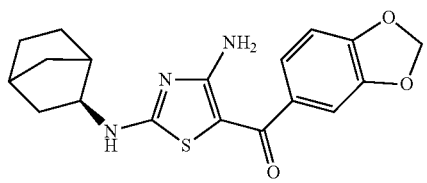 [SMILES: Nc1nc(N[C@H]2CC3CCC2C3)sc1C(=O)c1ccc2c(c1)OCO2]

Step 1: Synthesis of (4-amino-2-(methylthio)thiazol-5-yl)(benzo[d][1,3]dioxol-5-yl)methanone (36)

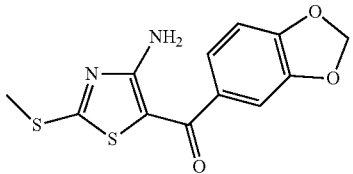 [SMILES: CSc1nc(N)c(C(=O)c2ccc3c(c2)OCO3)s1]

Prepared using the same procedure as described for compound 16 substituting 4-bromo-(1,2-methylenedioxy)benzene in place of 2-bromo-1-(2,3-dihydro-1,4-benzodioxin-6-yl)ethan-1-one to afford compound 36 as an orange solid. $^1$H NMR (400 MHz, CDCl$_3$) δ 7.36 (dd, J=8.04 Hz, J=1.72 Hz, 1H), 7.27 (d, J=1.68 Hz, 1H), 6.84 (d, J=8.08 Hz, 1H), 6.04 (s, 2H), 2.66 (s, 3H); ESIMS: m/z 295.0 [(M+H)$^+$].

Step 2: Synthesis of (4-amino-2-((2S)-bicyclo[2.2.1]heptan-2-ylamino)thiazol-5-yl)(benzo[d][1,3]dioxol-5-yl)methanone (30)

Prepared from compound 36 using the same procedure as described for compound 17 to afford the compound 30 as an orange-yellow glassy solid. $^1$H NMR (400 MHz, CD$_3$OD) δ 7.24 (dd, J=8.04 Hz, J=1.72 Hz, 1H); 7.13 (d, J=1.64 Hz, 1H), 6.86 (d, J=8.04 Hz, 1H), 6.01 (s, 2H), 2.32 (m, 2H), 1.81 (m, 1H), 1.14-1.62 (m, 8H); ESIMS: m/z 358.1 [(M+H)$^+$].

Example 2: Identification of Novel Epigenetic Compounds

To screen the compounds of this invention for epigenetic anti-cancer activity we used the YB5 cell-based system, which is derived from the human colon cancer cell line SW48 (Si et al., 2010, Cancer Res. 70:6968-6977; Raynal et al., 2012, Cancer Res. 72:1170-1181). YB5 cells contain a single insertion of cytomegalovirus (CMV) promoter driving green fluorescent protein (GFP) gene. GFP expression is silenced in >99.9% of YB5 cells by epigenetic mechanisms. In YB5 cells, the inserted GFP gene behaves similarly to endogenous tumor suppressor genes (TSGs) silenced by epigenetic mechanisms, and it can be reactivated by epigenetic anti-cancer agents such as DNA methylation inhibitors and/or HDAC inhibitors such as HDACi depsipeptide (Si et al., 2010, Cancer Res. 70:6968-6977; Raynal et al., 2012, Cancer Research, 72:1170-1181; Wu et al., 2008, Mol. Cell Biol, 28:3219-3235). Thus, reactivation of GFP expression and the resulting fluorescence is a measure of epigenetic anti-cancer activity.

The following procedure may be employed to identify compounds with the aforementioned utility. YB5 cells cultured in L-15 medium supplemented with 10% fetal bovine serum and 1% P/S are treated for 24 hours with varying concentrations (50 nM, 100 nM, 500 nM, 1 uM, 5 uM, 10 uM 25 uM and 50 uM) of test compounds. After treatment, cells are trypsinized and re-suspended in cell culture media with propidium iodide (PI) to stain dead cells. Reactivation of GFP is measured using flow cytometry to identify the GFP positive population. The relative activities are expressed as the percent of the response compared to treatment with 20 nM HDACi depsipeptide for 24 hours. YB5 cells are grown in 1% $CO_2$ atmosphere at 37° C.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A compound of formula (I):

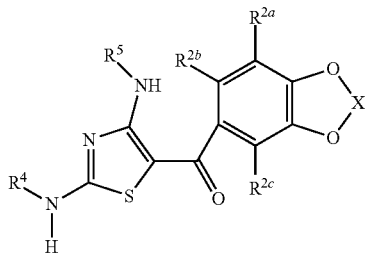

or an enantiomer, diastereomer, hydrate, solvate, and pharmaceutically acceptable salt thereof;
wherein in formula (I):
X is selected from the group consisting of

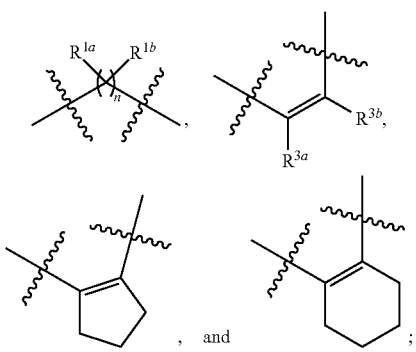

n is 2, 3 or 4;
$R^{1a}$ and $R^{1b}$ are at each occurrence independently selected from the group consisting of hydrogen, $C_{1-4}$ linear alkyl, and $C_{3-6}$ branched alkyl, or $R^{1a}$ and $R^{1b}$ are taken together with the atoms to which they are bound to form a three to six membered carbocyclic ring, or two $R^{1a}$ units on adjacent carbon atoms are taken together with the atoms to which they are bound to form a three to six membered carbocyclic ring;
$R^{2a}$, $R^{2b}$, and $R^{2c}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxy, $C_{1-6}$ haloalkoxy, thiol, $C_{1-6}$ linear thioalkyl, $C_{3-6}$ branched thioalkyl, cyano, nitro, and $NH_2$;
$R^{3a}$ and $R^{3b}$ are each independently selected from the group consisting of hydrogen, $C_{1-4}$ linear alkyl, and $C_{3-6}$ branched alkyl;

$R^4$ is selected from the group consisting of $C_{1-6}$ optionally substituted linear alkyl, $C_{3-7}$ optionally substituted branched alkyl, $C_{3-10}$ optionally substituted cycloalkyl, $C_{4-9}$ optionally substituted heteroaryl, $C_{4-9}$ optionally substituted heteroarylalkyl,

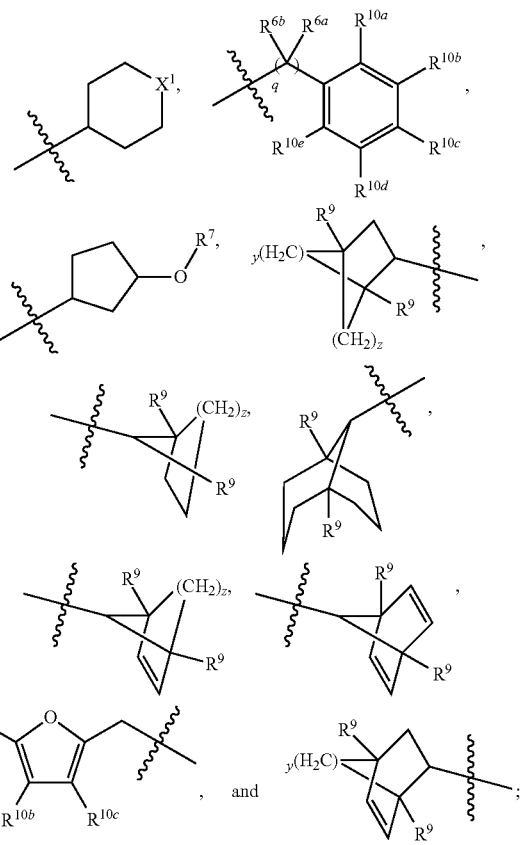

$X^1$ is selected from the group consisting of O, $NR^{11}$, S, SO, and $SO_2$;
$R^5$ is selected from the group consisting of hydrogen, $C_{1-6}$ linear alkyl, $C_{3-7}$ branched alkyl, $C_{3-7}$ cycloalkyl, and $COR^8$;
$R^{6a}$ and $R^{6b}$ are at each occurrence independently selected from the group consisting of hydrogen, $C_{1-6}$ linear alkyl, and $C_{3-6}$ branched alkyl;
q is 1 or 2;
$R^7$ is selected from the group consisting of $C_{1-6}$ linear alkyl, $C_{3-6}$ branched alkyl, $CF_3$, and $C_{1-3}$ haloalkyl;
$R^8$ is selected from the group consisting of hydrogen, $C_{1-6}$ linear alkyl, $C_{3-7}$ branched alkyl, $C_{1-6}$ linear alkoxy, $C_{3-7}$ branched alkoxy, and $C_{3-7}$ cycloalkyl;
$R^9$ at each occurrence is independently selected from the group consisting of hydrogen, methyl, ethyl, and n-propyl;
$R^{10a}$, $R^{10b}$, $R^{10c}$, $R^{10d}$, and $R^{10e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxyl, $C_{1-6}$ haloalkoxy, thiol, $C_{1-6}$ linear thioalkyl, $C_{3-6}$ branched thioalkyl, cyano, nitro, $NH_2$, and $NR^{11a}R^{11b}$;
$R^{11}$ is selected from the group consisting of hydrogen and $C_{1-6}$ linear alkyl;

$R^{11a}$ and $R^{11b}$ are each independently selected from the group consisting of $C_{1-6}$ linear alkyl and $C_{3-6}$ branched alkyl;

y is 1, 2, or 3; and z is 1, 2, or 3.

2. The compound of claim 1, wherein the compound of formula (I) is a compound of the formula selected from the group consisting of formula (II) and formula (IV)-(XVIII):

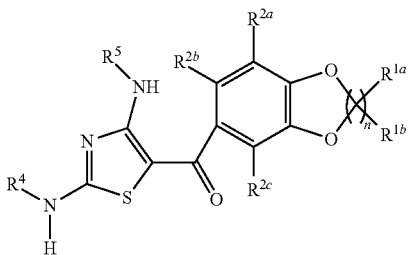
(II)

or an enantiomer, diastereomer, hydrate, solvate, and pharmaceutically acceptable salt thereof;

wherein in formula (II):
$R^{1a}$, $R^{1b}$, $R^{2a}$, $R^{2b}$, $R^{2c}$, $R^4$, $R^5$, and n are as defined in formula (I);

or an enantiomer, diastereomer, hydrate, solvate, and pharmaceutically acceptable salt thereof;

wherein in formula (III):
$R^{1a}$, $R^{1b}$, $R^{2a}$, $R^{2b}$, $R^{2c}$, $R^4$, $R^5$, and n are as defined in formula (I);

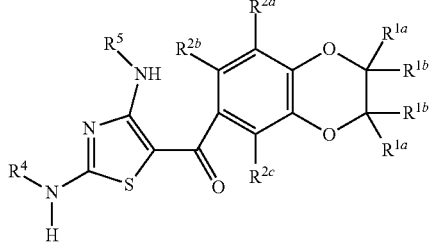
(IV)

or an enantiomer, diastereomer, hydrate, solvate, and pharmaceutically acceptable salt thereof;

wherein in formula (IV):
$R^{1a}$, $R^{1b}$, $R^{2a}$, $R^{2b}$, $R^{2c}$, $R^4$, and $R^5$ are as defined in formula (I);

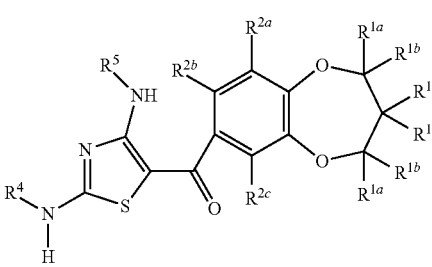
(V)

or an enantiomer, diastereomer, hydrate, solvate, and pharmaceutically acceptable salt thereof;

wherein in formula (V):
$R^{1a}$, $R^{1b}$, $R^{2a}$, $R^{2b}$, $R^{2c}$, $R^4$, and $R^5$ are as defined in formula (I);

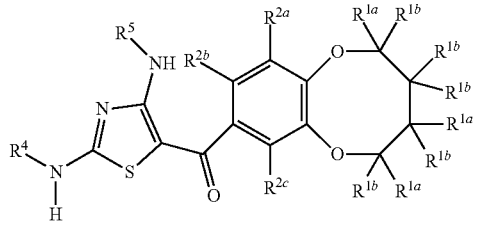
(VI)

or an enantiomer, diastereomer, hydrate, solvate, and pharmaceutically acceptable salt thereof;

wherein in formula (VI):
$R^{1a}$, $R^{1b}$, $R^{2a}$, $R^{2b}$, $R^{2c}$, $R^4$, and $R^5$ are as defined in formula (I);

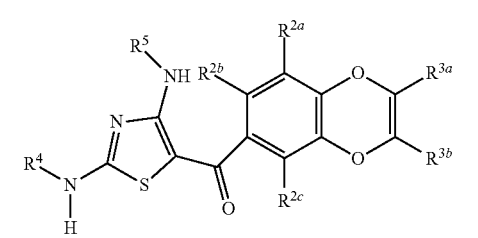
(VII)

or an enantiomer, diastereomer, hydrate, solvate, and pharmaceutically acceptable salt thereof;

wherein in formula (VII):
$R^{2a}$, $R^{2b}$, $R^{2c}$, $R^{3a}$, $R^{3b}$, $R^4$, and $R^5$ are as defined in formula (I);

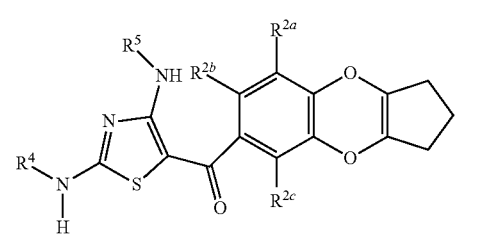
(VIII)

or an enantiomer, diastereomer, hydrate, solvate, and pharmaceutically acceptable salt thereof;

wherein in formula (VIII):
$R^{2a}$, $R^{2b}$, $R^{2c}$, $R^4$, and $R^5$ are as defined in formula (I);

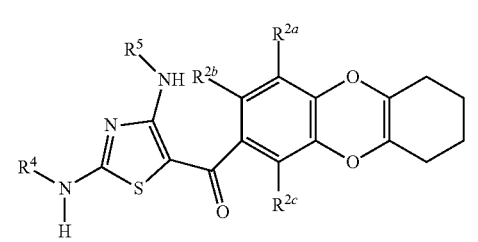
(IX)

or an enantiomer, diastereomer, hydrate, solvate, and pharmaceutically acceptable salt thereof;

wherein in formula (IX):
$R^{2a}$, $R^{2b}$, $R^{2c}$, $R^4$, and $R^5$ are as defined in formula (I);

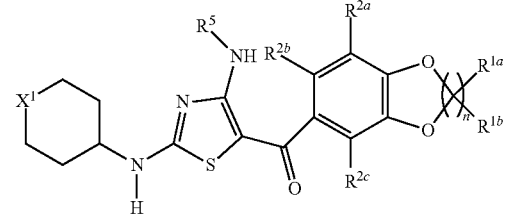
(X)

or an enantiomer, diastereomer, hydrate, solvate, and pharmaceutically acceptable salt thereof;

wherein in formula (X):
$R^{1a}$, $R^{1b}$, $R^{2a}$, $R^{2b}$, $R^{2c}$, $R^5$, $X^1$, and n are as defined in formula (I);

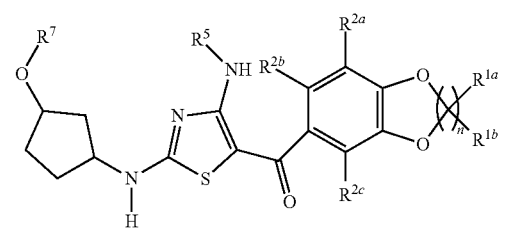
(XI)

or an enantiomer, diastereomer, hydrate, solvate, and pharmaceutically acceptable salt thereof;

wherein in formula (XI):
$R^{1a}$, $R^{1b}$, $R^{2a}$, $R^{2b}$, $R^{2c}$, $R^5$, $R^7$, and n are as defined in formula (I);

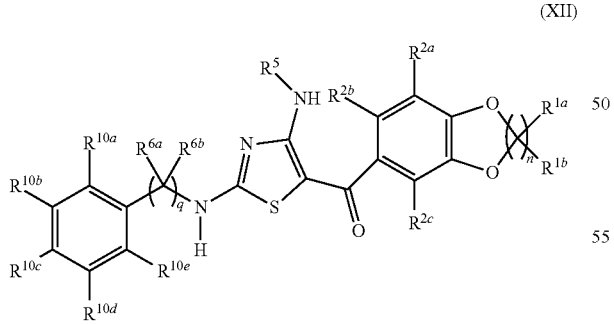
(XII)

or an enantiomer, diastereomer, hydrate, solvate, and pharmaceutically acceptable salt thereof;

wherein in formula (XII):
$R^{1a}$, $R^{1b}$, $R^{2a}$, $R^{2b}$, $R^{2c}$, $R^5$, $R^9$, n, y, and n are as defined in formula (I);

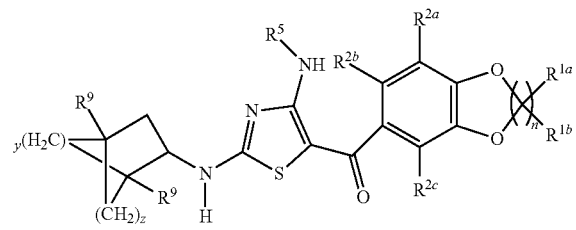
(XIII)

or an enantiomer, diastereomer, hydrate, solvate, and pharmaceutically acceptable salt thereof;

wherein in formula (XIII):
$R^{1a}$, $R^{1b}$, $R^{2a}$, $R^{2b}$, $R^{2c}$, $R^5$, $R^9$, n, y, and z are as defined in formula (I);

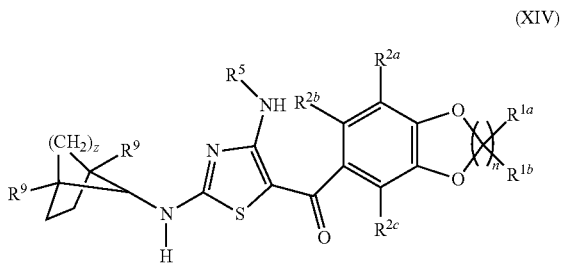
(XIV)

or an enantiomer, diastereomer, hydrate, solvate, and pharmaceutically acceptable salt thereof;

wherein in formula (XIV):
$R^{1a}$, $R^{1b}$, $R^{2a}$, $R^{2b}$, $R^{2c}$, $R^5$, $R^9$, n, and z are as defined in formula (I);

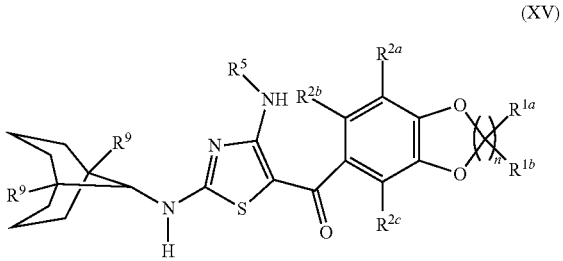
(XV)

or an enantiomer, diastereomer, hydrate, solvate, and pharmaceutically acceptable salt thereof;

wherein in formula (XV):
$R^{1a}$, $R^{1b}$, $R^{2a}$, $R^{2b}$, $R^{2c}$, $R^5$, $R^9$, and n are as defined in formula (I);

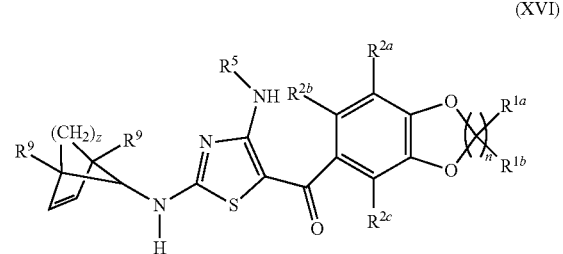
(XVI)

or an enantiomer, diastereomer, hydrate, solvate, and pharmaceutically acceptable salt thereof;

wherein in formula (XVI):
R$^{1a}$, R$^{1b}$, R$^{2a}$, R$^{2b}$, R$^{2c}$, R$^5$, R$^9$, n, and z are as defined in formula (I);

(XVII)

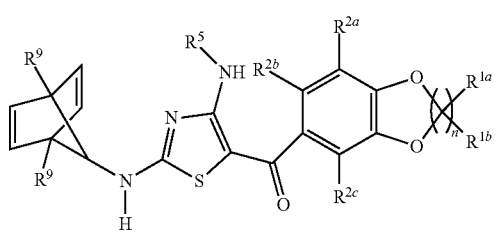

or an enantiomer, diastereomer, hydrate, solvate, and pharmaceutically acceptable salt thereof;
wherein in formula (XVII):
R$^{1a}$, R$^{1b}$, R$^{2a}$, R$^{2b}$, R$^{2c}$, R$^5$, R$^9$, and n are as defined in formula (I);

(XVIII)

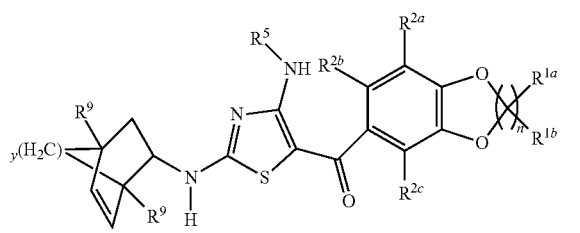

or an enantiomer, diastereomer, hydrate, solvate, and pharmaceutically acceptable salt thereof;
wherein in formula (XVIII):
R$^{1a}$, R$^{1b}$, R$^{2a}$, R$^{2b}$, R$^{2c}$, R$^5$, R$^9$, n, and y are as defined in formula (I).

3. A compound selected from the group consisting of:

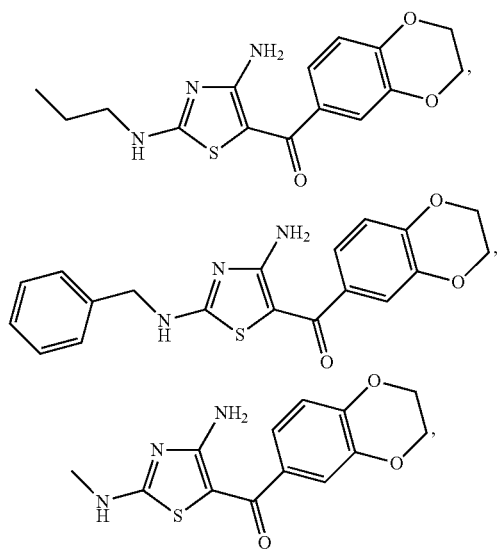

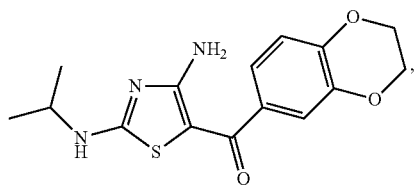

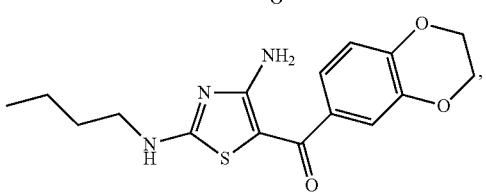

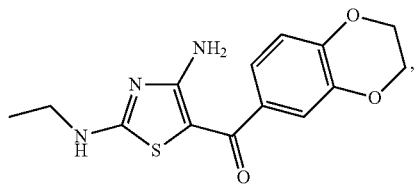

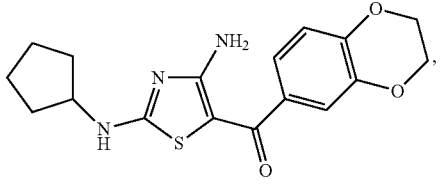

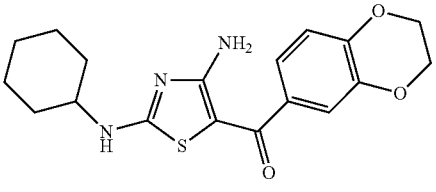

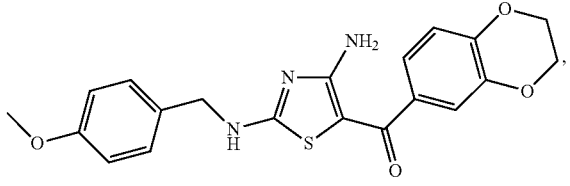

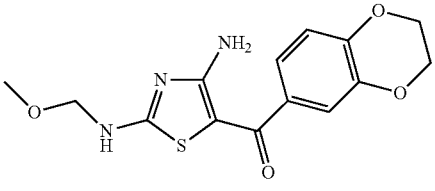

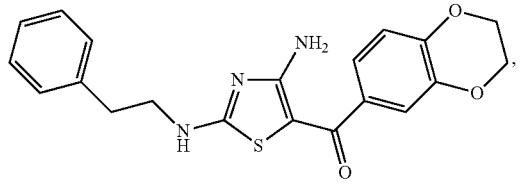

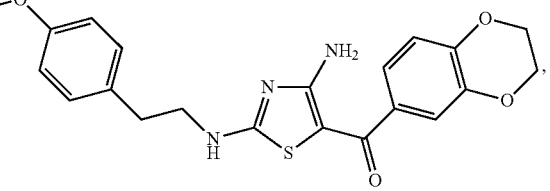

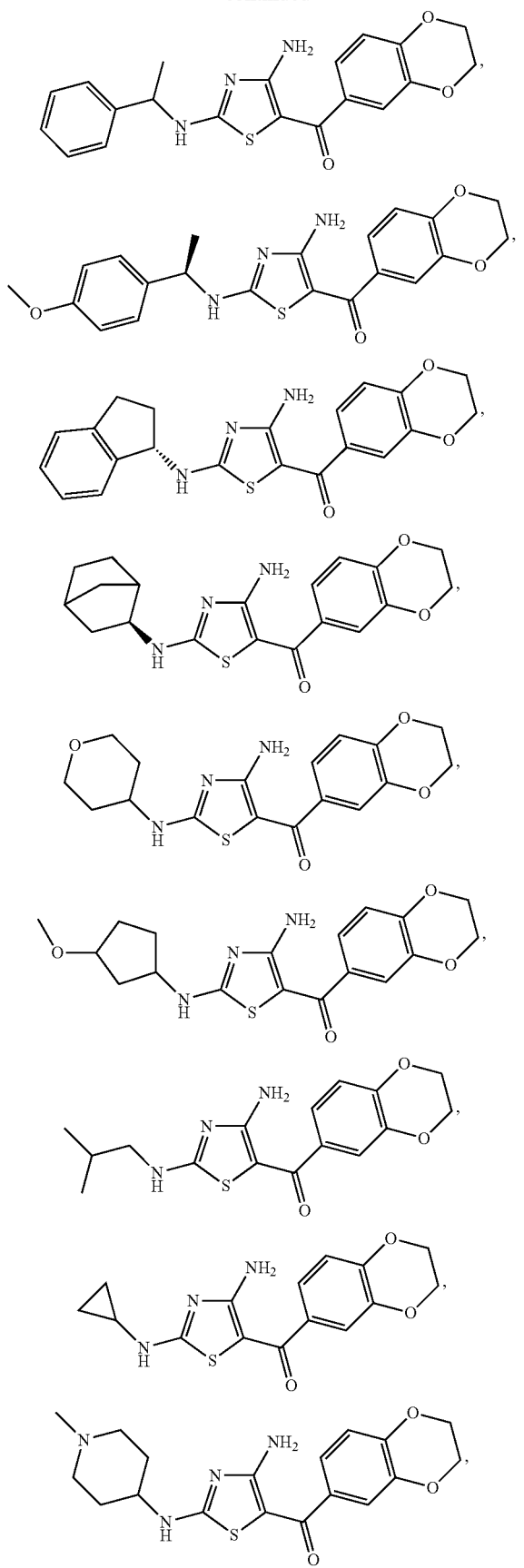
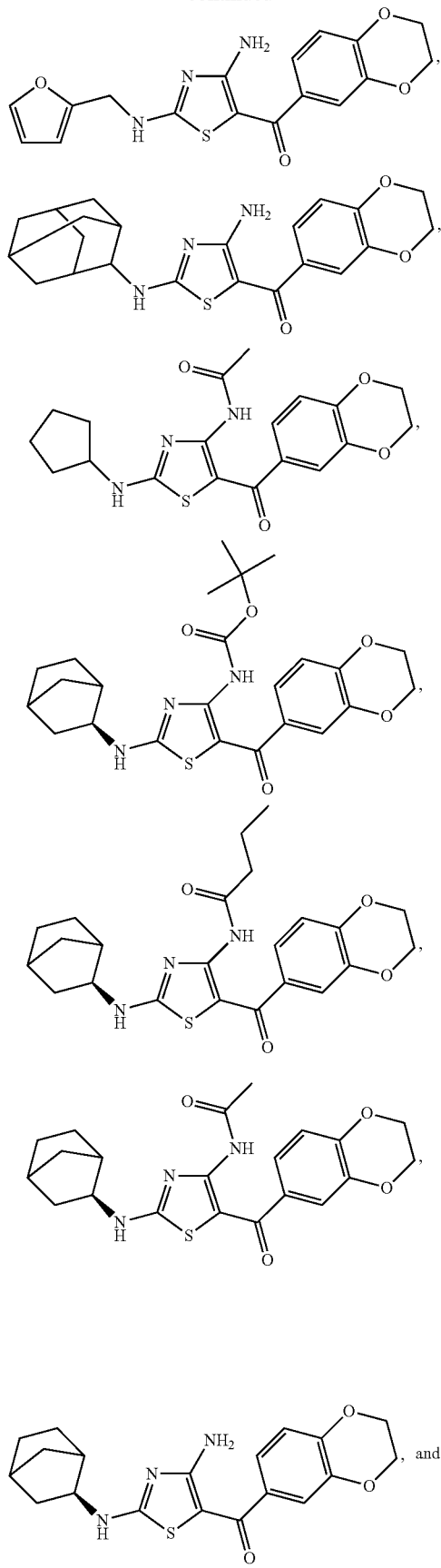

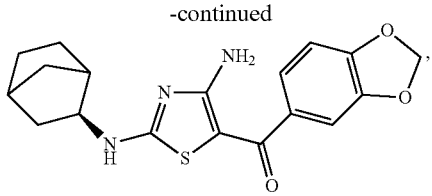
a pharmaceutically acceptable salt or solvate thereof, and any combinations thereof.
4. A composition comprising a compound of claim 1.
5. The composition of claim 4, wherein the composition further comprises a pharmaceutically acceptable carrier.
* * * * *